(12) United States Patent
Kimberly et al.

(10) Patent No.: US 8,119,355 B2
(45) Date of Patent: *Feb. 21, 2012

(54) BIOMARKERS FOR CANCER SENSITIVITY AND USES THEREOF

(75) Inventors: Robert P. Kimberly, Birmingham, AL (US); Tong Zhou, Birmingham, AL (US); Takeshi Isoyama, Tokyo (JP)

(73) Assignee: The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,113

(22) Filed: Mar. 12, 2010

(65) Prior Publication Data

US 2010/0173338 A1  Jul. 8, 2010

Related U.S. Application Data

(62) Division of application No. 11/877,234, filed on Oct. 23, 2007, now Pat. No. 7,713,525.

(60) Provisional application No. 60/862,527, filed on Oct. 23, 2006.

(51) Int. Cl.
*G01N 33/53* (2006.01)

(52) U.S. Cl. ........................................ 435/7.1

(58) Field of Classification Search .................. None
See application file for complete search history.

(56) References Cited

FOREIGN PATENT DOCUMENTS

| WO | WO03/037913 | 5/2003 |
|---|---|---|
| WO | WO2005/012875 | 2/2005 |
| WO | WO2005/032495 | 4/2005 |
| WO | WO2006/017531 | 2/2006 |
| WO | WO2006/029224 | 3/2006 |

OTHER PUBLICATIONS

Duan et al (Anticancer Res, Jul.-Aug. 2002, 22(4): Abstract).*
Holdenrieder et al (Anticancer Research, 1999, 19:2721-2724).*
Buchsbaum et al (Clinical Cancer Research, Sep. 2003, 9:3731-3741).*
Tockman et al (Cancer Res., 1992, 52:2711s-2718s).*
Asaka et al., "Aldolase A isoenzyme levels in serum and tissues of patients with liver diseases," Gastroenterology 84:155-60 (1983).
Bi et al., "Proteomic analysis of colorectal cancer reveals alterations in metabolic pathways: Mechanism of tumorigenesis," Mol. Cell. Proteomics 5(6):1119-30 (2006).
Chang et al., "Peroxiredoxin-I is an autoimmunogenic tumor antigen in non-small cell lung cancer," FEBS Lett. 579:2873-7 (2005).
Chang et al., "Augmented expression of peroxiredoxin I in lung cancer," Biochem. Biophys. Res. Commun. 289:507-12 (2001).
Daly et al., "Blood level of phosphoglycerate kinase does not correlate with presence or extent of tumor," Int. J. Biol. Markers 19(2):170-2 (2004).
Duan et al, "Overexpression of human phosphoglycerate kinase I (PGKI) induces multidrug resistance phenotype," Anticancer Res. 22(4):1933-41 (2002).
Holdenrieder et al., "Apoptosis in serum of patients with solid tumors," Anticancer Res. 19:2721-4 (1999).
Holdenrieder et al., "Circulating nucleosomes predict the response to chemotherapy in patients with advanced non-small cell lung cancer," Clin. Cancer Res. 10:5981-7 (2004).
Ichikawa et al., "Tumoricidal activity of a novel anti-human DR5 monoclonal antibody without hepatocyte cytotoxicity," Nat. Med. 7:954-60 (2001).
Kinnula et al., "Overexpression of peroxiredoxins I, II, III, V and VI in malignant mesothelioma," J. Pathol. 196:316-23 (2002).
Kuroi et al., "Clinical significance of plasma nucleosome levels in cancer patients," Int. J. Oncol. 19:143-8 (2001).
Lay et al., "Phosphoglycerate kinase acts in tumor angiogenesis as a disulphide reductase," Nature 408:869-73 (2000).
Li et al., "Inducible resistance of tumor cells to tumor necrosis factor-related apoptosis-inducing ligand receptor 2-mediated apoptosis by generation of a blockade at the death domain function," Cancer Res. 66(17):8520-28 (2006).
Noh et al., "Overexpression of peroxiredoxin in human breast cancer," Anticancer Res. 21:2085-90 (2001).
Ojika et al., "Immunochemical and immunohistochemical studies on three aldolase isozymes in human lung cancer," Cancer 67:2153-8 (1991).
Ono et al., "Acetylated histone H4 is reduced in human gastric adenomas and carcinomas," J. Exp. Clin. Cancer Res. 21(3):377-82 (2002).
Semenza et al., "Transcriptional regulation of genes encoding glycolytic enzymes by hypoxia-inducible factor," J. Biol. Chem. 269:23757-23763 (1994).
Tockman et al., "Considerations in bringing a cancer biomarker to clinical application," Cancer Res. 52:2711s-8s (1992).
Unwin et al., "Proteomic changes in renal cancer and co-ordinate demonstration of both the glycolytic and mitochondrial aspects of the Warburg effect," Proteomics 3:1620-32 (2003).
Yanagawa et al., "Peroxiredoxin I expression in human thyroid tumors," Cancer Lett. 145:127-32 (1999).

* cited by examiner

*Primary Examiner* — Sean Aeder
(74) *Attorney, Agent, or Firm* — McKeon, Meunier, Carlin & Curfman LLC

(57) ABSTRACT

Disclosed herein are biomarkers and uses thereof for evaluating anti-cancer efficacy and sensitivity.

9 Claims, 6 Drawing Sheets

FIG. 7A  FIG. 7B
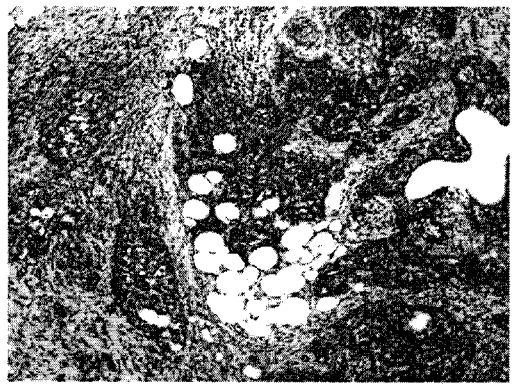
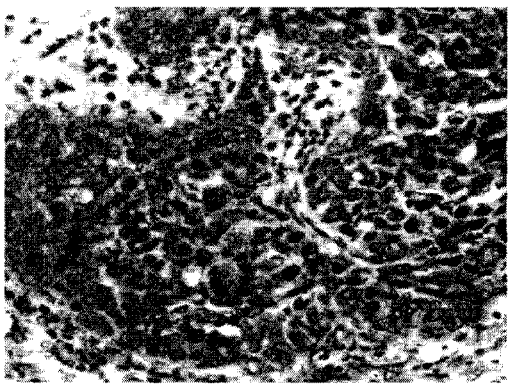
FIG. 7C
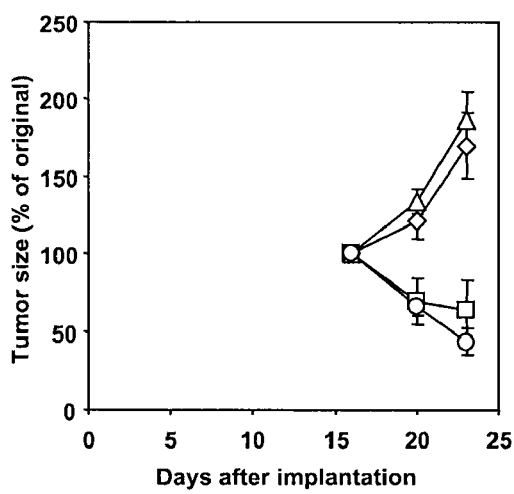
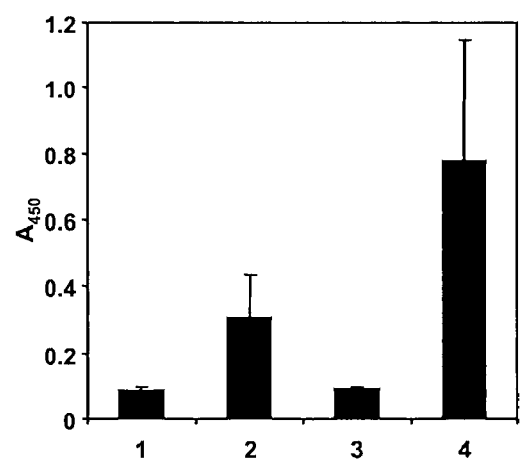
FIG. 8A  FIG. 8B

BIOMARKERS FOR CANCER SENSITIVITY AND USES THEREOF

CROSS-REFERENCE TO RELATED APPLICATIONS

The present application is a divisional application of U.S. Ser. No. 11/877,234, filed Oct. 23, 2007, which claims priority to U.S. Ser. No. 60/862,527, filed Oct. 23, 2006. These applications are is incorporated by reference herein in their entireties.

STATEMENT REGARDING FEDERALLY SPONSORED RESEARCH

This invention was made with government support under Grant Nos. P50 CA83591, P5089019 and P20 CA101955 awarded by the National Institutes of Health. The government has certain rights in the invention.

BACKGROUND OF THE INVENTION

The profile of serum tumor-associated proteins is useful as a biomarker in detecting cancer at early stages, monitoring disease progression, and determining therapeutic response. Drug-responsive biomarkers are particularly critical for the selection of patients in whom the drug efficacy is expected. Currently, there are no serum biomarkers available for evaluation of the early tumor cell response during DR5-mediated apoptosis.

In many cases of anticancer therapies, biomarkers are critical to predict efficacy of the therapy for individual subjects. Biomarkers can be used to predict efficacy before treatment or can be monitored to predict the therapeutic response shortly after initiation of treatment. These biomarkers are useful to select appropriate subjects for the therapy and to save remaining subjects, in whom the therapy is unlikely to exhibit any clinical benefit, from unnecessary side effects and costs. Therefore, it becomes requisite to discover predictive biomarkers for anticancer drug development. Nevertheless, there are only a few biomarkers available for determining treatment, although many effective cancer therapies have been developed. For example, expression of estrogen receptor and/or progesterone receptors in breast cancers can predict therapeutic response to tamoxifen. Breast cancers with overexpression of the HER2/neu (ErbB2) proto-oncogene are more likely to respond to a humanized anti-HER2 monoclonal antibody trastuzumab (Herceptin).

Tumor necrosis factor (TNF)-related apoptosis-inducing ligand (TRAIL), also called Apo2L, is a member of the TNF superfamily and has an ability to trigger apoptosis in a variety of transformed cell lines. Five receptors for TRAIL have been identified: two death receptors, DR4 (TRAIL-R1) and DR5 (TRAIL-R2), that transduce the apoptosis signal, and three decoy receptors, DcR1 (TRAIL-R3), DcR2 (TRAIL-R4), and osteoprotegrin, that inhibit TRAIL-induced apoptosis. DR4 and DR5 contain a cytoplasmic death domain that is essential for induction of apoptosis. After binding of TRAIL to DR4 and/or DR5, these receptors initiate apoptosis through recruitment of the adaptor Fas-associated death domain and the initiator caspase-8 to form the death-inducing signaling complex, which leads to activation of the effector caspase cascade and eventual cell death.

TRAIL induces apoptosis only in tumorigenic or transformed cells, but not in normal cells, although TRAIL mRNA is expressed constitutively in many human normal tissues. It is suggested that there may be some mechanisms that protect normal cells from apoptosis induced by TRAIL. Preclinical studies in mice and nonhuman primates have shown that recombinant soluble TRAIL has an antitumor efficacy in various human tumor xenograft models and no significant toxicity to normal tissues. However, it has also been reported that some forms of recombinant soluble TRAIL induce apoptosis in normal human hepatocytes in vitro, suggesting potential liver toxicity in humans, although it may be caused by the form of recombinant soluble TRAIL. The anti-human DR5 monoclonal antibody TRA-8 and humanized versions of TRA-8 induce apoptosis in cancer cells both in vitro and in vivo, without hepatocellular toxicity. However, various degrees of sensitivity have been observed among cancer cells.

SUMMARY OF THE INVENTION

As embodied and broadly described herein, this disclosure relates to biomarkers for evaluating the efficacy of anti-cancer therapies or treatments. In addition, biomarkers are provided for evaluation of tumor cell response during DR5-mediated apoptosis. Provided are methods of predicting sensitivity of a cancer cell to therapeutic agents, of predicting efficacy of therapeutic agents and of determining an effective dose of a therapeutic agent by detecting a biomarker such as phosphoglycerate kinase 1 (PGK1), fructose-bisphosphate aldolase A (ALDOA), peroxiredoxin 1 (PRDX1), cofilin-1 (COF1) and histone H4 (H4)

Additional advantages of the disclosed method and compositions are in the description which follows, and in part are understood from the description, or may be learned by practice of the disclosed method and compositions. The advantages of the disclosed method and compositions are realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 2 shows the effect of TRA-8 on candidate biomarkers in culture supernatant of colon cancer cells.

FIG. 3 shows the effect of TRA-8 on candidate biomarkers in culture supernatant of breast cancer cells.

FIG. 4 shows the effect of TRA-8 on candidate biomarkers in culture supernatant of lung cancer cells.

FIG. 5 shows the time course of candidate biomarkers in the culture supernatant upon TRA-8 treatment.

FIG. 6 shows the effect of chemotherapeutic agents on candidate biomarkers in culture supernatant of cancer cells.

FIG. 7 shows expression of PRDX1 and PGK1 in human cancer cell lines and tissues. FIG. 7A shows Western blot analysis of PRDX1 expression in cancer cells and FIG. 7B shows Western blot analysis of PGK1 expression in cancer cells: proteins of total cell lysates from 13 human cancer cell lines were separated in SDS-PAGE, and the blots were probed with specific monoclonal antibodies against human PRDX1 and PGK1. The lanes shown in FIGS. 7A and 7B correspond to the following cell lines, Lane 1, MDA231; Lane 2, UL-3A; Lane 3, UL-3C; Lane 4, COLO205; Lane 5, HT29; Lane 6, SW480; Lane 7, SW620; Lane 8, SW116; Lane 9, WiDR; Lane 10, 2-LMP; Lane 11, BT474; Lane 12, H2122; Lane 13, A427. FIG. 7C shows immunohistological staining of PGK1 in human ovarian cancer tissue. Paraffin section of a human ovarian cancer tissue was stained with an anti-PGK1 monoclonal antibody.

FIG. 8 shows the release of candidate biomarkers from TRA-8 and CPT-11 treated COLO 205 tumors in a xenograft model. FIG. 8A shows the effects of TRA-8 and CPT-11 treatment on athymic nude mice bearing COLO 205 tumors. TRA-8 (10 mg/kg) was administered to mice on days 16 and 20. CPT-11 (33 mg/kg) was administered to mice on days 17 and 21. Each point and bar represent the mean and standard error of tumor size data of each group treated with none (diamonds), TRA-8 (squares), CPT-11 (triangles) or TRA-8 in combination with CPT-11 (circles), respectively. FIG. 8B shows candidate biomarkers detected in sera obtained from the tumor-bearing mice treated with none (column 1), TRA-8 (column 2), CPT-11 (column 3) or TRA-8 plus CPT-11 (column 4) on day 20. PRDX1 level in the sera was determined as $A_{450}$ value using ELISA. Each column and bar represents the mean and standard error of the data, respectively.

DETAILED DESCRIPTION OF THE INVENTION

Figure 1A:
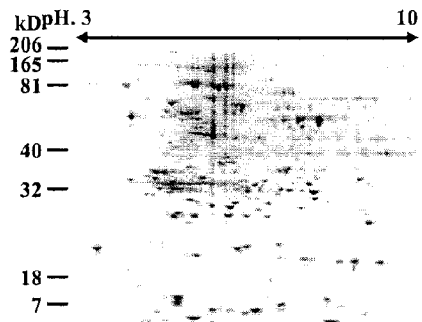
FIG. 1 shows effect of TRA-8 on COLO 205 cells. COLO 205 cells were treated with none (A) or TRA-8 at a final concentration of 10 (B), 100 (C), or 1000 ng/ml (D) in serum-free conditions. The culture supernatants were resolved by two-dimensional gel electrophoresis with subsequent staining with SYPRO® Ruby (Molecular Probes, Carlsbad, Calif.). Positions of molecular mass markers are shown on the left of each figure. The range of isoelectric point is shown on the top of each figure. Circles represent analyzed proteins.
Figure 1B:
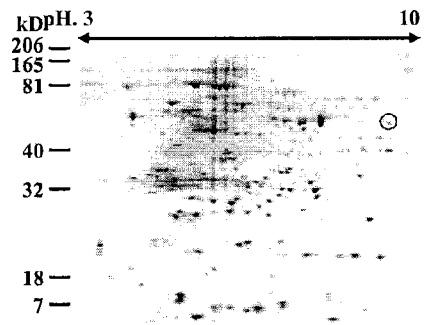
Figure 1C:
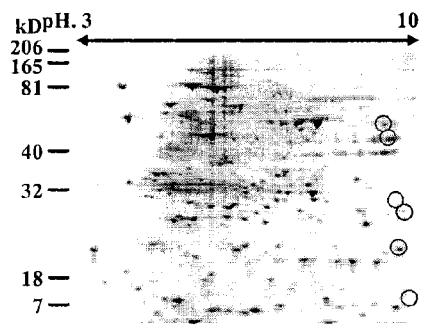
Figure 1D:
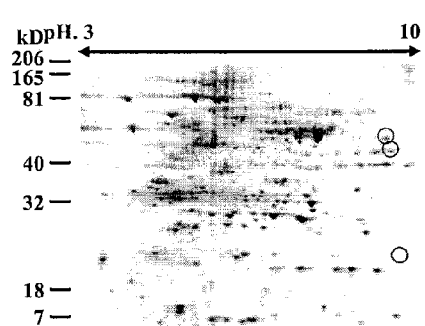

Biomarkers, which predict therapeutic response, are essential for development of anticancer therapy. As described herein, monitoring anticancer drug effects leads to prediction of the therapeutic response. Two-dimensional gel electrophoresis (2-DE) and mass spectrometry (MS) were used to identify proteins that monitor and predict the effect of cancer therapies. As described herein phosphoglycerate kinase 1 (PGK1), fructose-bisphosphate aldolase A (ALDOA), peroxiredoxin 1 (PRDX1), cofilin-1 (COF1) and histone H4 (H4) are released from cancer cells in response to therapeutic agents. The release of these candidate biomarkers was correlated with the cytotoxic effect of chemotherapy agents such as CPT-11, oxaliplatin and paclitaxel. Furthermore, when DR5 agonists and CPT-11 were administered twice to tumor-bearing mice, PRDX1 level in the sera was increased by the DR5 agonist alone or in combination with CPT-11. The protein set identified and described herein comprises biomarkers useful to monitor and predict the efficacy of anti-cancer drugs.

Disclosed herein are biomarkers and methods for identifying and using the biomarkers. By biomarker is meant any assayable characteristics or compositions that is used to identify, predict, or monitor a condition (e.g., a tumor or other cancer, or lack thereof) or a therapy for said condition in a subject or sample. A biomarker is, for example, a protein or combination of proteins whose presence, absence, or relative amount is used to identify a condition or status of a condition in a subject or sample. In one particular example, a biomarker is a protein or combination of proteins whose relative concentration in a subject or sample is characteristic of sensitivity of a cancer cell to a therapeutic agent. Biomarkers identified herein are measured to determine levels, expression, activity, or to detect variants. Variants include amino acid or nucleic acid variants or post translationally modified variants.

Disclosed herein is the use of fructose-bisphosphate aldolase A (ALDOA) as a biomarker for predicting sensitivity of a cancer cell to an anti-cancer agent. Aldolase enzymes catalyze the cleavage of structurally related sugar phosphates, including fructose-1-phosphate (F-1-P), which is an intermediate of fructose metabolism. Three isoforms of the enzyme have been identified namely aldolase A (isolated from muscle), aldolase B (isolated from liver) and aldolase C (isolated from brain). Aldolase A (Fructose-bisphosphate aldolase (muscle-type aldolase)) is a ubiquitous glycolytic enzyme that catalyzes the reversible cleavage of fructose 1,6-biphosphate to glyceraldehyde 3-phosphate and dihydroxyacetone phosphate. Aldolase is transcriptionally induced by hypoxia inducible factor-1 (HIF-1) in pancreatic cancer cells. Aldolase A is found in the developing embryo and is produced in even greater amounts in adult muscle. Aldolase A expression is repressed in adult liver, kidney and intestine and similar to aldolase C levels in brain and other nervous tissue. Alternative splicing of this gene results in multiple transcript variants that encode the same protein. The anaerobic metabolism-associated genes Glut1 and aldolase A are highly expressed in tumor cells with constitutive expression of HIF-1α, rendering these cells resistant to apoptosis induced by hypoxia and glucose deprivation. Cancer cells employ glycolytic enzymes to produce ATP anaerobically in response to hypoxia. The enhanced expression of Glut-1 and aldolase A mRNAs under hypoxia is abrogated by dominant-negative HIF-1α (dnHIF-1α) transfectants, rendering the pancreatic cancer cells sensitive to apoptosis and growth inhibition induced by hypoxia or glucose deprivation. ALDOA is overexpressed in lung cancer and hepatocellular carcinoma compared with normal tissues and is detected in the sera of cancer patients.

Disclosed herein is the use of phosphoglycerate kinase 1 (PGK1) as a biomarker for predicting sensitivity of a cancer cell to an anti-cancer agent. Phosphoglycerate kinase 1 (PGK1), also known as ATP:3-phosphoglycerate 1-phosphotransferase, catalyzes the reversible conversion of 1,3-diphosphoglycerate to 3-phosphoglycerate, generating one molecule of ATP. Disulfide bonds in secreted proteins are considered to be inert because of the oxidizing nature of the extracellular milieu. An exception to this rule is a reductase secreted by tumor cells that reduces disulfide bonds in the serine proteinase, plasmin. Reduction of plasmin initiates proteolytic cleavage in the kringle 5 domain and release of the tumor blood vessel inhibitor angiostatin. New blood vessel formation or angiogenesis is critical for tumor expansion and metastasis. The plasmin reductase isolated from conditioned medium of fibrosarcoma cells is the glycolytic enzyme phosphoglycerate kinase. Recombinant phosphoglycerate kinase had the same specific activity as the fibrosarcoma-derived protein. Plasma of mice bearing fibrosarcoma tumors contained several-fold more phosphoglycerate kinase, as compared with mice without tumors. Administration of phosphoglycerate kinase to tumor-bearing mice caused an increase in plasma levels of angiostatin and a decrease in tumor vascularity and rate of tumor growth. Phosphoglycerate kinase not only functions in glycolysis but is also secreted by tumor cells and participates in the angiogenic process as a disulfide reductase. However, according to Daly et al., blood level of phosphoglycerate kinase is not thought to correlate with the presence or extent of a tumor (Daly E B et al., *Int. J. Biol. Markers* 19(2):170-2 2004). PGK1 is transcriptionally activated by HIF-1. Increased levels of PGK1 were found in renal call carcinoma compared with patient-matched normal kidney cortex. PGK1 was secreted from various cultured cancer cells and the plasma of HT1080 fibrosarcoma tumor-bearing mice contained several-fold more PGK1 than mice without the tumors.

Disclosed is the use of peroxiredoxin 1 (PRDX1) as a biomarker for predicting sensitivity of a cancer cell to an anti-cancer agent. Peroxiredoxin 1 (PRDX1) is a member of the peroxiredoxin family of antioxidant enzymes that reduce oxidants such as hydrogen peroxide to non-reactive species in the cell. The protein encoded by PRDX1 is thought to play a protective role in the cell indicated by both its antioxidative nature and its role in T-cell antiviral activity. However, PRDX1 may also aid in cancer proliferation. There are correlations between the expression level and the stage of tumor progression in squamous cell carcinoma of the oral cavity; high expression in follicular thyroid tumors, but not in papillary carcinoma of the thyroid. PRDX1 is induced by oxidative stress and constitutively expressed in most human cells and is induced to higher levels upon serum stimulation in untransformed and transformed cells. Elevated levels of PRDX1 were observed in thyroid cancer, breast cancer, lung cancer, malignant mesothelioma and non-small lung cancer patients.

Disclosed is the use of cofilin 1 (COF1) as a biomarker for predicting sensitivity of a cancer cell to an anti-cancer agent. Cofilin is a widely distributed intracellular actin-modulating protein that binds and depolymerizes filamentous F-actin and inhibits the polymerization of monomeric G-actin in a pH-dependent manner. It is involved in the translocation of actin-cofilin complex from cytoplasm to nucleus. COF1 is a non-muscle isoform of actin-depolymerizing factor/colfilins, which are small actin-binding proteins that regulate actin polymerization and depolymerization and sever actin filaments. COF1 is widely distributed in various tissues. Cofilin activity is regulated through a variety of mechanisms including phosphorylation. Increased levels of cofilin were observed in renal cell carcinoma due to infiltrating T-lymphocyte expressing cofilin, as compared with patient-matched normal kidney section.

Disclosed is the use of histone H4 as a biomarker for predicting sensitivity of a cancer cell to an anti-cancer agent. Histones are basic nuclear proteins that are responsible for the nucleosome structure of the chromosomal fiber in eukaryotes. Nucleosomes consist of approximately 146 base pairs of DNA wrapped around a histone octamer composed of pairs of each of the four core histones (H2A, H2B, H3, and H4). The chromatin fiber is further compacted through the interaction of a linker histone, H1, with the DNA between the nucleosomes to form higher order chromatin structures. When cell death occurs, nucleosomes are released into the circulation and are detected in elevated amounts in serum or plasma. Elevated level of circulating nucleosomes was detected in sera or plasma of patients with various solid tumors as compared to healthy persons. In addition, the temporal increase of circulating nucleosomes after chemotherapy or radiotherapy was observed. Changes of circulating nucleosomes in patients with advanced non-small cell lung cancer during chemotherapy can predict therapeutic response. As demonstrated by Ono et al., *J. Exp. Clin. Cancer Res.* 21(3):377-82 (2002), the levels of acetylated histone H4 expression are reduced in gastric carcinomas in comparison with non-neoplastic mucosa. Acetylated histone H4 is detected in the nuclei of both non-neoplastic epithelial and stromal cells, whereas the levels of acetylated histone H4 are reduced in gastric carcinomas and gastric adenomas. Reduced expression of acetylated histone H4 has also been observed in some areas of intestinal metaplasia adjacent to carcinomas. Reduction in the expression of acetylated histone H4 has been significantly correlated with advanced stage, depth of tumor invasion and lymph node metastasis. Thus, low levels of histone acetylation is closely associated with the development and progression of gastric carcinomas, possibly through alteration of gene expression.

Provided herein is a method of predicting sensitivity of a cancer cell to an anti-cancer agent comprising contacting the cancer cell with an effective amount of the anti-cancer agent and evaluating the release by the cell of one or more of the herein disclosed biomarkers. The cancer cell are contacted in vitro or in vivo.

An increase in release of the herein provided biomarkers by the contacted cell compared to a control cell indicates that the cancer cell is sensitive to the agent. By increased release is meant any increase in the amount of the biomarker that is detectable outside of the cell as compared to native or control levels. Thus, the increase is about 1, 5, 10, 20, 30, 40, 50, 60, 70, 80, 90, 100%, or any amount of increase in between or higher as compared to native or control levels.

For example, a cancer cell or cells, such as from a biopsy from a subject, is contacted in vitro with an anti-cancer agent in a culture medium. The presence or absence of the herein disclosed biomarkers is measured in the culture medium. This measurement is compared to results of other control cancer and non-cancer cells and to results using other anti-cancer agents.

Release of biomarkers are optionally evaluated in a xenograft model. For example, human tissue is transplanted to an immunodeficient mouse. The presence or absence of the herein disclosed biomarker(s) is measured in a bodily fluid before and/or after treatment with an anti-cancer agent.

Release of biomarkers is optionally evaluated in a subject or a sample from a subject. The presence or absence of the herein disclosed biomarker(s) is measured in a tissue (e.g., biopsy) or bodily fluid. Bodily fluids that used to evaluate the presence or absence of the herein disclosed biomarkers include without limitation blood, urine, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid. For example, levels of biomarker are measured in the blood or biopsy before and after treatment in a subject.

Biopsy refers to the removal of a sample of tissue for purposes of diagnosis. For example, a biopsy is from a cancer or tumor, including a sample of tissue from an abnormal area or an entire tumor. A non-limiting list of different types of cancers include lymphoma, B cell lymphoma, T cell lymphoma, mycosis fungoides, Hodgkin's Disease, myeloid leukemia, bladder cancer, brain cancer, nervous system cancer, head and neck cancer, kidney cancer, lung cancers such as small cell lung cancer and non-small cell lung cancer, brain cancers such as neuroblastoma and glioblastoma, ovarian cancer, pancreatic cancer, prostate cancer, liver cancer, melanoma, squamous cell carcinomas, cervical carcinoma, breast cancer, renal cancer, genitourinary cancer, esophageal carcinoma, hematopoietic cancers, testicular cancer, or colon and rectal cancers.

As used herein, subject is a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. As used herein, patient or subject are used interchangeably and refer to a subject with a disease or disorder. The term patient or subject includes human and veterinary subjects.

The disclosed methods involve comparing the release of the disclosed biomarkers from a cancer cell to the release of the same biomarkers in a control sample. It is understood that the control sample is a non-cancer cell concurrently run, or a standard created by assaying one or more non-cancer cells and collecting the biomarker data. Thus, the control sample is optionally a standard that is created and used continuously. The standard includes, for example, the average level of release of a biomarker by a non-cancer cell(s) or any other control group. The cancer cell optionally is contacted with an anti-cancer agent prior to the detection of the biomarkers. Thus, a control sample is a cancer cell that is not contacted with an anti-cancer agent or a cancer cell prior to contact with the anti-cancer agent.

Also provided is a method of predicting or monitoring the efficacy of an anti-cancer agent in a subject. The method comprises acquiring a biological sample, such as tissue or bodily fluid, from the subject after administering the agent to the subject. For example, the tissue or bodily fluid is collected from the subject 1 to 60 minutes, hours, days, or weeks after administering the agent to the subject. The method further comprises detecting levels of one or more biomarkers selected from the group consisting of ALDOA, PGK1, PRDX1, COF1, and histone H4 in the biological sample. An increase in level(s) of one or more biomarkers is evidence of treatment efficacy. Thus, a decline in said increase or time is evidence of decreasing efficacy. Thus, it is preferred that biological samples be systematically acquired over time to monitor changes in biomarker levels.

Also provided is a method of determining an effective dose for an anti-cancer agent. The method comprises contacting one or more cancer cells with a plurality of dosages of the anti-cancer agent. The conditions of the disclosed method preferably allow cellular release of one or more of the herein disclosed biomarkers. The method further comprises detecting the release of one or more of the disclosed biomarkers at each dosage. As disclosed herein, higher biomarker release rates indicate an effective dosage. At least one cell is contacted with more than one dosage or each cell is contacted with only one dosage.

The anti-cancer agent of the disclosed methods comprise, for example, a death receptor agonist. By death receptor is meant a receptor that induces cellular apoptosis once bound by a ligand. Death receptors include, for example, tumor necrosis factor (TNF) receptor superfamily members having death domains (e.g., TNFRI, Fas, DR3, 4, 5, 6) and TNF receptor superfamily members without death domains LTβR, CD40, CD27, HVEM. Thus, the death receptor agonist is selected from the group consisting of a DR5 antibody, DR4 antibody, Fas Ligand, TNF, and TNF-related apoptosis-inducing ligand (TRAIL). The DR5 antibody is optionally TRA-8 or an antibody having the same epitope specificity as TRA-8. The DR5 antibody is optionally a humanized version of TRA-8.

Signal transduction through, for example, DR5 is a key mechanism in the control of DR5-mediated apoptosis. A common feature of the death receptors of the TNFR superfamily is that they all have a conserved death domain in their cytoplasm tail (Zhou, T., et al. 2002. Immunol Res 26:323-336). It is well established that DR5-mediated apoptosis is initiated at the death domain. Crosslinking of DR5 at the cell surface by TRAIL or agonistic anti-DR5 antibody leads to oligomerization of DR5, which is immediately followed by the recruitment of FADD to the death domain of DR5 (Bodmer, J. L., et al. 2000. Nat Cell Biol 2:241-243; Chaudhary, P. M., et al. 1997. Immunity 7:821-830; Kuang, A. A., et al. 2000. J Biol Chem 275:25065-25068; Schneider, P., et al. 1997. Immunity 7:831-836; Sprick, M. R., et al. 2000. Immunity 12:599-609). The death-domain engaged FADD further recruits the initiator procaspase 8 and/or procaspase 10 to form a DISC through homophilic DD interactions (Krammer, P. H. 2000. Nature 407:789-795). The activated caspase 8 and 10 may activate caspase 3 directly, or cleave the BH3-containing protein Bid to activate a mitochondria-dependent apoptosis pathway through release of cytochrome C and caspase 9 activation (Desagher, S., and J. C. Martinou. 2000. Trends Cell Biol 10:369-377; Scaffidi, C., et al. 1998. Embo J 17:1675-1687). Following the formation of the death domain complex, several signal transduction pathways are activated such as caspase, NF-κB, and JNK/p38. Activation of these signaling pathways leads to regulation of death receptor-mediated apoptosis through the Bcl-2 and IAP family of proteins.

By agonist is meant a substance (molecule, drug, protein, etc.) that is capable of combining with a receptor (e.g., a death receptor) on a cell and initiating the same reaction or activity typically produced by the binding of the endogenous ligand (e.g., apoptosis). The agonist of the present method, for example, is a death receptor ligand, such as TNF, Fas Ligand, or TRAIL. The agonist includes a fragment of these ligands comprising the death receptor binding domain such that the fragment is capable of binding and activating the death receptor. The agonist includes a fusion protein comprising the death receptor binding domain such that the fusion protein is capable of binding and activating the death receptor. The agonist includes a polypeptide having an amino acid sequence with at least 85-99% homology (including, e.g., 90%, 95% and 99% homology) to TNF, Fas or TRAIL such that the homologue is capable of binding and activating the death receptor.

The agonist includes an apoptosis-inducing antibody that binds the death receptor. The antibody is optionally monoclonal, polyclonal, chimeric, single chain, humanized, fully human antibody, or any Fab or F(ab')2 fragments thereof. By apoptosis-inducing antibody is meant an antibody that causes programmed cell death either before or after activation using the methods provided herein. Thus, the agonist of the present method includes an antibody specific for a Fas, TNFR1 or TRAIL death receptor, such that the antibody activates the death receptor. The agonist includes an antibody specific for DR4 or DR5. For example, the agonist is a DR5 antibody having the same epitope specificity as or is secreted by, a mouse-mouse hybridoma having ATCC Accession Number PTA-1428 (e.g., the TRA-8 antibody), ATCC Accession Number PTA-1741 (e.g., the TRA-1 antibody), ATCC Accession Number PTA-1742 (e.g., the TRA-10 antibody). The mouse-mouse hybridoma TRA-8 was deposited with the American Type Culture Collection, 10801 University Boulevard, Manassas, Va. 20110-2209 in accordance with the Budapest Treaty on Mar. 1, 2000, and has the accession number PTA-1428. The agonist is optionally an antibody having the same epitope specificity, or secreted by, the hybridoma having ATCC Accession Number PTA-3798 (e.g., the 2E12 antibody).

The antibody is optionally derived using transformant $E.$ $coli$ strains designated as $E.\ coli$ JM109/pHA15 (harboring a plasmid carrying cDNA encoding the H1-type heavy chain of humanized TRA-8), $E.\ coli$ JM109/pHB14 (harboring a plasmid carrying cDNA encoding the heavy chain of humanized TRA-8), $E.\ coli$ JM109/pHC10 (harboring a plasmid carrying cDNA encoding the H3-type heavy chain of humanized TRA-8), $E.\ coli$ JM109/pHD21 (harboring a plasmid carrying cDNA encoding the H4-type heavy chain of humanized TRA-8), and $E.\ coli$ JM109/pM11 (harboring a plasmid carrying cDNA encoding the heavy chain of chimeric TRA-8), $E.\ coli$ DH5☐/pHSG/M1-2-2 (harboring a plasmid carrying cDNA encoding a fusion fragment of the variable region of the humanized LM1 TRA-8 light chain and the constant region of human Ig☐ chain). These strains were deposited with International Patent Organism Depositary, National Institute of Advanced Industrial Science and Technology, 1-1, Higashi 1 chome Tsukuba-shi, Ibaraki-ken, 305-5466, Japan on Apr. 20, 2001, in accordance with the Budapest Treaty for the Deposit of Microorganisms, and were accorded the accession numbers FERM BP-7555, FERM BP-7556, FERM BP-7557, FERM BP-7558, FERM BP-7559, and FERM BP-7562, respectively.

The TRAIL receptor targeted by the antibody of the present method includes DR4 or DR5. Such receptors are described in published patent applications WO99/03992, WO98/35986, WO98/41629, WO98/32856, WO00/66156, WO98/46642, WO98/5173, WO99/02653, WO99/09165, WO99/11791, WO99/12963 and published U.S. Pat. No. 6,313,269, which are all incorporated herein by reference in their entirety for the receptors taught therein. Monoclonal antibodies specific for these receptors are generated using methods known in the art. See, e.g., Kohler and Milstein, Nature, 256:495-497 (1975) and Eur. J. Immunol. 6:511-519 (1976), both of which are hereby incorporated by reference in their entirety for these methods. See also methods taught in published patent application WO01/83560, which is incorporated herein by reference in its entirety.

The anti-cancer agent of the disclosed methods is optionally an anti-cancer compound such as a chemotherapeutic drug. Generally, an anti-cancer compound is a compound or composition effective in inhibiting or arresting the growth of an abnormally growing cell. Illustrative examples of anti-cancer compounds include bleomycin, carboplatin, chlorambucil, cisplatin, colchicine, CPT-11, cyclophosphamide, daunorubicin, dactinomycin, diethylstilbestrol doxorubicin, etoposide, 5-fluorouracil, floxuridine, melphalan, methotrexate, mitomycin, 6-mercaptopurine, oxaliplatin, paclitaxel, teniposide, 6-thioguanine, vincristine and vinblastine. Further examples of anti-cancer compounds and therapeutic agents are found in The Merck Manual of Diagnosis and Therapy, 18th Ed., Beers et al., eds., 2006, Whitehouse Station, N.J. and Sladek et al. Metabolism and Action of Anti-Cancer Drugs, 1987, Powis et al. eds., Taylor and Francis, New York, N.Y.

According to the American Cancer Society, there are 5 main categories of chemotherapy drugs. They are alkylating agents, nitrosureas, antimetabolites, antitumor antibiotics, and mitotic inhibitors. Alkylating agents work directly on the cancer cell's DNA to prevent it from replicating. Busulfan, cyclophoshamide and melphalan are examples of alkylating agents. Nitrosureas inhibit a cancer cell's enzymes needed for DNA repair. Carmustine and lomustine are examples of nitrosureas. Antimetabolites interfere with both a cancer cell's DNA and RNA. 5-Fluorouracil, methotrexate and fludarabine are examples of antimetabolites. Antitumor antibiotics also interfere with a cancer cell's DNA in addition to changing its cellular membrane—the outside layer of protective coating. Bleomycin, doxorubicin and idarubicin are examples of antitumor antibiotics. Mitotic inhibitors are plant alkaloids that inhibit enzymes needed for protein synthesis in the cancer cell. Docetaxel, etoposide and vinorelbine are examples of mitotic inhibitors.

Certain methods disclosed herein involve collecting a biological sample from a subject. The collection of biological samples is performed by standard methods. Typically, once a sample is collected, the biomarkers are detected and measured. The disclosed biomarkers are detected using any suitable technique. Further, molecules that interact with or bind to the disclosed biomarkers, such as antibodies to a biomarker, are detected using known techniques. Many suitable techniques—such as techniques generally known for the detection of proteins, peptides and other analytes and antigens—are known, some of which are described below. In general, these techniques involve direct imaging (e.g., microscopy), immunoassays, or functional determination. By functional determination is meant that a given biomarker, such as a protein that has a function are detected by the detection of said function. For example, an enzyme is detected by evaluating its activity on its substrate.

Immunodetection methods are used for detecting, binding, purifying, removing and quantifying various molecules including the disclosed biomarkers. Further, antibodies and ligands to the disclosed biomarkers are detected. For example, the disclosed biomarkers are employed to detect antibodies having reactivity therewith. Standard immunological techniques are described, e.g., in Hertzenberg, et al., Weir's Handbook of Experimental Immunology, vols. 1-4 (1996); Coligan, Current Protocols in Immunology (1991); Methods in Enzymology, vols. 70, 73, 74, 84, 92, 93, 108, 116, 121, 132, 150, 162, and 163; and Paul, Fundamental Immunology (3d ed. 1993), each of which is incorporated herein by reference in its entirety and specifically for teachings regarding immunodetection methods.

The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (MA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that is bound by the antibody, as the case may be, under conditions effective to allow the formation of immunocomplexes. Contacting a sample with the antibody to the molecule of interest or with the molecule that is bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, is washed to remove any non-specifically bound antibody species, allowing only those antibodies specifically bound within the primary immune complexes to be detected.

Immunoassays include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label includes a fluorescent dye, a member of a binding pair, such as biotin/streptavidin, a metal (e.g., gold), or an epitope tag that specifically interacts with a molecule to be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally used in the practice of the invention as they are detected at very low amounts. Fluorophores are compounds or molecules that luminesce. Typically fluorophores absorb electromagnetic energy at one wavelength and emit electromagnetic energy at a second wavelength. In the case where multiple antigens are reacted with a single array, each antigen is labeled with a distinct fluorescent compound for simultaneous detection. Labeled spots on the array are detected using a fluorimeter, the presence of a signal indicating an antigen bound to a specific antibody.

Labeling is either direct or indirect. In direct labeling, the detecting antibody (the antibody for the molecule of interest) or detecting molecule (the molecule that is bound by an antibody to the molecule of interest) includes a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme is attached to or associated with the detecting antibody or detecting molecule. The signal-generating molecule then generates a detectable signal at the site of the immunocomplex. For example, an enzyme, when supplied with suitable substrate, produces a visible or detectable product at the site of the immunocomplex. ELISAs use this type of indirect labeling.

As another example of indirect labeling, an additional molecule (which is referred to as a binding agent) that can bind to either the molecule of interest or to the antibody (primary antibody) to the molecule of interest, such as a second antibody to the primary antibody, is contacted with the immunocomplex. The additional molecule optionally has a label or signal-generating molecule or moiety. The additional molecule is, for example, an antibody, which is termed a secondary antibody. Binding of a secondary antibody to the primary antibody forms a so-called sandwich with the first (or primary) antibody and the molecule of interest. The immune complexes contacted with the labeled, secondary antibody under conditions effective and for a period of time sufficient to allow the formation of secondary immune complexes. The secondary immune complexes are generally washed to remove any non-specifically bound labeled secondary antibodies, and the remaining label in the secondary immune complexes can then be detected. The additional molecule includes one of a pair of molecules or moieties that can bind to each other, such as the biotin/avidin pair. In this mode, the detecting antibody or detecting molecule includes the other member of the pair.

Other modes of indirect labeling include the detection of primary immune complexes by a two step approach. For example, a molecule (which is referred to as a first binding agent), such as an antibody, that has binding affinity for the molecule of interest or corresponding antibody is used to form secondary immune complexes, as described above. After washing, the secondary immune complexes is contacted with another molecule (which is referred to as a second binding agent) that has binding affinity for the first binding agent, again under conditions effective and for a period of time sufficient to allow the formation of immune complexes (thus forming tertiary immune complexes). The second binding agent is linked to a detectable label or signal-generating molecule or moiety, allowing detection of the tertiary immune complexes thus formed. This system provides for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance is found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab−Ag]n), and reagent antigens are used to detect specific antibody ([Ab−Ag]n). If the reagent species is previously coated onto cells (as in hemagglutination assay) or very small particles (as in latex agglutination assay), clumping of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual label (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand Immunosensors allow the easy investigation of kinetic interactions and, with the advent of specialized instruments, offer wide application in immunoanalysis.

The use of immunoassays to detect a specific protein involves, for example, the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix, for example, is stained and used for scanning, autoradiography or storage. In addition, the most commonly used support matrices—agarose and polyacrylamide—provide a means of separating molecules by size, in that they are porous gels. A porous gel acts as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easier to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by wrapping around the polypeptide backbone and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE using proteins of known molecular weight along with the protein to be characterized. A linear relationship exists between the logarithm of the molecular weight (MW) of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing is used for the first dimension, conveniently carried out in a tube gel, and SDS electrophoresis in a slab gel is used for the second dimension. One example of a procedure is that of O'Farrell, P. H., High Resolution Two-dimensional Electrophoresis of Proteins, J. Biol. Chem. 250:4007-4021

(1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods.

Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis are found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, are used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens is readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding are conjugated, for example, with anti-immunoglobulins, conjugated staphylococcal Protein A, which binds IgG, or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders), for example, are run simultaneously in order to approximate molecular mass of the protein of interest in a heterogeneous sample.

The gel shift assay or electrophoretic mobility shift assay (EMSA) are used to detect the interactions between DNA binding proteins and their cognate DNA recognition sequences, in both a qualitative and quantitative manner. Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts are incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe is either double-stranded or single-stranded. For the detection of DNA binding proteins such as transcription factors, either purified or partially purified proteins, or nuclear cell extracts are used. For detection of RNA binding proteins, either purified or partially purified proteins, or nuclear or cytoplasmic cell extracts are used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions.

Gel shift methods include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions include phosphoric, sulfuric, and nitric acids, and acid violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Fan Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (MA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) are also measured if coupled to larger carrier proteins (e.g., bovine gamma-globulin or human serum albumin) capable of inducing antibody formation. MA involves mixing a radioactive antigen (because of the ease with which iodine atoms are introduced into tyrosine residues in a protein, the radioactive isotopes $^{125}$I or $^{131}$I are often used) with antibody to that antigen. The antibody is generally linked to a solid support, such as a column or beads. Unlabeled or cold antigen is then added in known quantities, and the amount of labeled antigen displaced is measured. Initially, the radioactive antigen is bound to the antibodies. When cold antigen is added, the two compete for antibody binding sites. At higher concentrations of cold antigen, more binds to the antibody, displacing the radioactive variant. The bound antigens are separated from the unbound ones in solution and the radioactivity of each used to plot a binding curve. The technique is both extremely sensitive and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which is detected, for example, by spectrophotometric, fluorometric or visual means. Enzymes that are used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are know to those of skill in the art. In one variation, antibodies that bind to proteins are immobilized onto a selected surface exhibiting protein affinity, such as a well in a polystyrene microtiter plate. Then, a test composition suspected of containing a marker antigen is added to the wells. After binding and washing to remove non-specifically bound immunocomplexes, the bound antigen is detected. Detection is achieved, for example, by the addition of a second antibody specific for the target protein, which is linked to a detectable label. This type of ELISA is a simple sandwich ELISA. Detection also is achieved by the addition of a second antibody, followed by the addition of a third antibody that has binding affinity for the second antibody, with the third antibody being linked to a detectable label.

Another variation is a competition ELISA. In competition ELISAs, test samples compete for binding with known amounts of labeled antigens or antibodies. The amount of reactive species in the sample is determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunocomplexes. Antigen or antibodies are linked to a solid support, such as in the form of plate, beads, dipstick, membrane or column matrix, and the sample to be analyzed applied to the immobilized antigen or antibody. In coating a plate with either antigen or antibody, one generally incubates the wells of the plate with a solution of the antigen or antibody, either overnight or for a specified period of hours. The wells of the plate are then washed to remove incompletely adsorbed material. Any remaining available surfaces of the wells are coated with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure is optionally used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunocomplex then requires a labeled secondary binding agent or a secondary binding agent in conjunction with a labeled third binding agent.

Under conditions effective to allow immunocomplex (antigen/antibody) formation means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions mean that the incubation is at a temperature and for a period of time sufficient to allow effective binding. Incubation steps are typically from about 1 minute to twelve hours, at temperatures of about 20° to 30° C., or incubated overnight at about 0° C. to about 10° C.

Following all incubation steps in an ELISA, the contacted surface is washed so as to remove non-complexed material. A washing procedure includes washing with a solution such as PBS/Tween or borate buffer. Following the formation of specific immunocomplexes between the test sample and the originally bound material, and subsequent washing, the occurrence of even minute amounts of immunocomplexes are determined.

To provide a detecting means, the second or third antibody has, for example, an associated label to allow detection, as described above. This is optionally an enzyme that generates color development upon incubating with an appropriate chromogenic substrate. Thus, for example, one contacts and incubates the first or second immunocomplex with a labeled antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is optionally quantified, e.g., by incubation with a chromogenic substrate such as urea and bromocresol purple or 2,2'- azido-di-(3-ethyl-benzthiazoline-6-sulfonic acid [ABTS] and $H_2O_2$, in the case of peroxidase as the enzyme label. Quantitation is achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software is adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays are used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, optionally in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods are automated for high throughput production. For capture arrays and protein function analysis, it is important that proteins be correctly folded and functional; this is not always the case, e.g., where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension are also used as the basis of arrays, providing they are coded for identification; systems include color coding for microbeads (Luminex, Austin, Tex.; Bio-Rad Laboratories), semiconductor nanocrystals (e.g., QDOTS™, Quantum Dot, Hayward, Calif.), barcoding for beads (ULTRAPLEX™ beads, SmartBead Technologies Ltd, Babraham, Cambridge, UK) and multimetal microrods (e.g., NANOBARCODES™ particles, Nanoplex Technologies, Mountain View, Calif.). Beads are optionally assembled into planar arrays on semiconductor chips (LEAP S™ technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control. It may or may not alter the functional properties of the protein, and reproducibility and efficiency are variable. Covalent coupling methods provide a stable linkage, are applied to a range of proteins and have good reproducibility. However, orientation is variable. Furthermore, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately, and the array may require special handling and have variable stability.

Several immobilization chemistries and tags have been described for fabrication of protein arrays. Substrates for covalent attachment include glass slides coated with amino- or aldehyde-containing silane reagents. In the VERSALINX™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HYDROGEL™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx, Inc., Hayward, Calif.) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences, Affymetrix Inc. and Genetix] as well as manual equipment [e.g., V & P Scientific]. Bacterial colonies are optionally robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Nanosciences Inc. and Nanolink Inc., for example, have developed commercially available nanoarrays.

Fluorescence labeling and detection methods are widely used. The same instrumentation as used for reading DNA microarrays is applicable to protein arrays. For differential display, capture (e.g., antibody) arrays are probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity is amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity is achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven, Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; Bioinvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) are optionally useful in arrays.

The term scaffold refers to ligand-binding domains of proteins, which are engineered into multiple variants capable of binding diverse target molecules with antibody-like properties of specificity and affinity. The variants are produced in a genetic library format and selected against individual targets by phage, bacterial or ribosome display. Such ligand-binding scaffolds or frameworks include Affibodies based on *S. aureus* protein A (Affibody, Bromma, Sweden), Trinectins based on fibronectins (Phylos, Lexington, Mass.) and Anticalins based on the lipocalin structure (Pieris Proteolab, Freising-Weihenstephan, Germany). These are used on capture arrays in a similar fashion to antibodies and have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure (SomaLogic, Boulder, Colo.) and their interaction with protein is enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains are used to detect binding.

Protein analytes binding to antibody arrays are detected directly or indirectly, for example, via a secondary antibody. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately. Serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through molecular imprinting technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which is useful diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and are used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g., via a His tag and immobilized. Cell free protein transcription/translation is a viable alternative for synthesis of proteins which do not express well in bacterial or other in vivo systems.

For detecting protein-protein interactions, protein arrays are in vitro alternatives to the cell-based yeast two-hybrid system and are useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale proteome chips are also useful in identification of functional interactions, drug screening, etc. (Proteometrix, Branford, Conn.).

As a two-dimensional display of individual elements, a protein array is used to screen phage or ribosome display libraries, in order to select specific binding partners, including antibodies, synthetic scaffolds, peptides and aptamers. In this way, library against library screening is carried out. Screening of drug candidates in combinatorial chemical libraries against an array of protein targets identified from genome projects is another application of the approach.

Multiplexed bead assays use a series of spectrally discrete particles that are used to capture and quantitate soluble analytes. The analyte is then measured by detection of a fluorescence-based emission and flow cytometric analysis. Multiplexed bead assays generate data that is comparable to ELISA based assays, but in a multiplexed or simultaneous fashion. Concentration of unknowns is calculated for the cytometric bead array as with any sandwich format assay, i.e., through the use of known standards and by plotting unknowns against a standard curve. Further, multiplexed bead assays allow quantification of soluble analytes in samples never previously considered due to sample volume limitations. In addition to the quantitative data, powerful visual images are generated revealing unique profiles or signatures that provide the user with additional information at a glance.

In some examples of the disclosed methods, when the level of expression of a biomarker(s) is assessed, the level is compared with the level of expression of the biomarker(s) in a reference standard. By reference standard is meant the level of expression of a particular biomarker(s) from a sample or subject lacking a cancer, at a selected stage of cancer, or in the absence of a particular variable such as a therapeutic agent. Alternatively, the reference standard comprises a known amount of biomarker. Such a known amount correlates with an average level of subjects lacking a cancer, at a selected stage of cancer, or in the absence of a particular variable such as a therapeutic agent. A reference standard also includes the expression level of one or more biomarkers from one or more selected samples or subjects as described herein. For example, a reference standard includes an assessment of the expression level of one or more biomarkers in a sample from a subject that does not have a cancer, is at a selected stage of progression of a cancer, or has not received treatment for a cancer. Another exemplary reference standard includes an assessment of the expression level of one or more biomarkers in samples taken from multiple subjects that do not have a cancer, are at a selected stage of progression of a cancer, or have not received treatment for a cancer.

When the reference standard includes the level of expression of one or more biomarkers in a sample or subject in the absence of a therapeutic agent, the control sample or subject is optionally the same sample or subject to be tested before or after treatment with a therapeutic agent or is a selected sample or subject in the absence of the therapeutic agent. Alternatively, a reference standard is an average expression level calculated from a number of subjects without a particular cancer. A reference standard also includes a known control level or value known in the art. In one aspect of the methods disclosed herein, it is desirable to age-match a reference standard with the subject diagnosed with a cancer.

In one technique to compare protein levels of expression from two different samples (e.g., a sample from a subject diagnosed with a cancer and a reference standard), each sample is separately subjected to 2D gel electrophoresis. Alternatively, each sample is differently labeled and both samples are loaded onto the same 2D gel. See, e.g., Unlu et al. Electrophoresis, 1997; 18:2071-2077, which is incorporated by reference herein for at least its teachings of methods to assess and compare levels of protein expression. The same protein or group of proteins in each sample is identified by the relative position within the pattern of proteins resolved by 2D electrophoresis. The expression levels of one or more proteins in a first sample is then compared to the expression level of the same protein(s) in the second sample, thereby allowing the identification of a protein or group of proteins that is expressed differently between the two samples (e.g., a biomarker). This comparison is made for subjects before and after they are suspected of having a cancer, before and after they begin a therapeutic regimen, and over the course of that regimen.

In another technique, the expression level of one or more proteins is in a single sample as a percentage of total expressed proteins. This assessed level of expression is compared to a preexisting reference standard, thereby allowing for the identification of proteins that are differentially expressed in the sample relative to the reference standard.

There are a variety of sequences related to biomarkers as well as any other protein disclosed herein that are disclosed on Genbank, and these sequences and others are herein incorporated by reference in their entireties as well as for individual subsequences contained therein. Thus, a variety of sequences are provided herein and these and others are found in Genbank. Those of skill in the art understand how to resolve sequence discrepancies and differences and to adjust the compositions and methods relating to a particular sequence to other related sequences. Primers and/or probes are designed for any sequence given the information disclosed herein and known in the art. For example, the gene sequence for human ALDOA is found at GenBank Accession No. NM_000034. The gene sequence for human PGK1 is found at GenBank Accession No. NM_000291. The gene sequence for human PRDX1 is found at GenBank Accession No. NM_002574. The gene sequence for human COF1 is found at GenBank Accession No. NM_005507. The gene sequence for human histone H4 is found at GenBank Accession No. NM_175054.

Also provided is a detection kit comprising antibodies specific for two or more of ALDOA, PGK1, PRDX1, COF1, and histone H4. Optionally, the detection kit comprises antibodies specific for ALDOA, PGK1, and PRDX1. Optionally, the detection kit comprises antibodies specific for two or more of ALDOA, PGK1, PRDX1, COF1, and histone H4, in an assay system. Kits, for example, further comprise instructions for performing the methods described herein. Such a kit optionally comprises a labeling means and/or a therapeutic agent.

Also provided is a multiplex assay system comprising a solid support and a detection means for determining the levels of two or more of ALDOA, PGK1, PRDX1, COF1, and histone H4 in a sample. The detection means is any known or newly discovered compositions or systems to determine the levels of ALDOA, PGK1, and PRDX1. For example, the detection means include antibodies or other ligands specific for the biomarkers. Solid supports include any useful form, such as thin films or membranes, beads, bottles, dishes, fibers, optical fibers, woven fibers, chips, compact disks, shaped polymers, particles and microparticles. A chip is a rectangular or square small piece of material. Preferred forms for solid-state substrates are thin films, beads, or chips.

EXAMPLES

Example 1

Materials and Methods

Antibodies: An agonistic anti-human DR5 antibody, TRA-8, was prepared as described in Ichikawa et al (Ichikawa et al., *Nat. Med.* 7:954-60 2001). Anti-ALDOA, anti-COF1, and anti-PGK1 antibodies were purchased from Santa Cruz Biotechnology, Inc. (Santa Cruz, Calif.). Anti-histone H4 and anti-PRDX1 antibodies were purchased from Upstate Group, Inc. (Charlottesville, Va.). Camptothecin derivative CPT-11 (Pfizer Inc., New York, N.Y.) and platinum compound oxaliplatin (Sanofi-Aventis, Bridgewater, N.J.) were obtained from the University of Alabama at Birmingham Hospital Pharmacy (Birmingham, Ala.). Taxoid paclitaxel was purchased from Sigma-Aldrich Co. (St. Louis, Mo.).

Cells: COLO 205 human colon cancer cells and NCI-H2122 human lung cancer cells were maintained in RPMI-1640 medium (Invitrogen, Carlsbad, Calif.) supplemented with 4.5 g/l glucose, 10 mM HEPES, 1 mM sodium pyruvate, and 10% heat-inactivated fetal bovine serum (FBS; HyClone Laboratories, Logan, Utah). WiDr human colon cancer cells and A-427 human lung cancer cells were cultured in Minimum essential medium (Invitrogen) supplemented with 0.1 mM non-essential amino acids, 1 mM sodium pyruvate, and 10% FBS. HT-29 human colon cancer cells were grown in RPMI-1640 medium supplemented with 10 mM HEPES, 1 mM sodium pyruvate, and 10% FBS. The 2LMP subclone of human breast cancer cell line MDA-MB-231 was maintained in Dulbecco's Modified Eagle Medium (Invitrogen) with 10% FBS. BT-474 human breast cancer cells were cultured in RPMI-1640 medium supplemented with 10 mg/ml insulin, 4.5 g/l glucose, 10 mM HEPES, 1 mM sodium pyruvate, and 10% FBS. All cell lines were grown at 37° C. in a humidified atmosphere of 5% $CO_2$.

Sample preparation of culture supernatant: For 2-DE, COLO 205 cells ($2 \times 10^6$ cells) were washed with phosphate-buffered saline prepared DPBS (Mediatech, Herndon, Va.) and incubated in the serum-starved condition at 37° C. for 24 hours. After washing with serum-free medium, the cells were treated with or without TRA-8 in 10 ml of serum-free medium at 37° C. for 24 hours. The culture supernatants were retrieved by centrifugation at 10,000×g for 30 min at 4° C., concentrated by Centriplus (Millipore, Billerica, Mass.), and precipitated with acetone. The precipitates were resolubilized in READYPREP™ rehydration/sample buffer (Bio-Rad Laboratories, Hercules, Calif.). For immunoblotting analysis, the cells ($1 \times 10^6$ cells) were plated and cultured in complete culture medium at 37° C. for 24 h. The cells were washed with serum-free medium and treated with or without TRA-8 or chemotherapeutic agents in 5 ml of serum-free media at 37° C. for 24 h. The culture supernatants were retrieved by centrifugation, concentrated, and precipitated with acetone. The precipitates were resolubilized in sodium dodecyl sulfate (SDS) sample buffer (62.5 mM Tris-HCl, pH 6.8, 5% 2-mercaptoethanol 2% SDS, 10% glycerol, and 0.002% bromophenol blue).

Two-dimensional gel electrophoresis: Culture supernatant samples were loaded onto READYSTRIP™ IPG strip, pH 3-10 (Bio-Rad Laboratories) by overnight passive rehydration. Isoelectric focusing (IEF) was performed using PROTEAN® IEF cell (Bio-Rad Laboratories). IEF voltage was applied according to the following paradigm: 250 V for 20 min, 8000 V for 2.5 h, and 8000 V to achieve 20 kVh. After IEF, strips were equilibrated in READYPREP™ equilibration buffer I (Bio-Rad Laboratories) at room temperature for 10 min, and then incubated in READYPREP™ equilibration buffer II (Bio-Rad Laboratories, Inc.) at room temperature for 10 min. Second dimension electrophoresis was carried out with CRITERION® Tris-HCl Gel, 8-16% (Bio-Rad Laboratories). The gels were stained with SYPRO® (Molecular Probes, Carlsbad, Calif.) Ruby protein gel stain (Bio-Rad Laboratories) according to the manufacturer's instructions.

Protein spot analysis and identification: PDQUEST® 2-D analysis software (Bio-Rad Laboratories) was used for spot detection and matching among gels. Selected spots were excised from gels, destained with 20 mM $NH_4HCO_3$ containing 50% $CH_3CN$, dehydrated with $CH_3CN$, and dried. The gel pieces were rehydrated and digested with 10 μl of 20 mM $NH_4HCO_3$, pH 8.0, containing 10 ng/ml sequencing grade modified trypsin (Promega Co., Madison, Wis.) at 37° C. for 12 h. The resulting peptides were extracted once with 0.05% formic acid and twice with 0.05% formic acid in $CH_3CN$. Pooled samples were evaporated to 2-3 added with 10 μl of 0.05% formic acid, and analyzed by liquid chromatography equipped with tandem MS (LC-MS/MS).

LC-MS/MS experiments were performed on a Q-T of Ultima API mass spectrometer (Waters Co., Milford, Mass.) equipped with a DiNa (KYA Technologies Co., Tokyo, Japan) using a homemade ESI tip column packed with Develosil ODS-HG (3 μm, Nomura Chemical Co., Ltd., Aichi, Japan). Elution of peptides was carried out with a linear gradient 0-35% $CH_3CN$ over 35 min at a flow rate of 200 nl/min. The volume of the samples was 5 μl. The MS/MS spectra were searched against the GenBank non-redundant protein database using Mascot (Matrix Science Inc., Boston, Mass.).

Immunoblotting analysis: Culture supernatant samples were resolved in SDS-polyacrylamide gel electrophoresis (PAGE), followed by immunoblotting. ALDOA, COF1, or PGK1 were detected with goat anti-ALDOA, anti-COF1, or anti-PGK1 antibodies and peroxidase conjugated rabbit anti-goat IgG (Southern Biotechnology Associates, Birmingham, Ala.), as primary and secondary antibodies, respectively. Histone H4 or PRDX1 were detected with anti-histone H4 or anti-PRDX1 antibodies and peroxidase-conjugated goat anti-rabbit IgG, mouse/human ads-HRP (Southern Biotechnology Associates), as primary and secondary antibodies, respectively. ECL Western blotting detection reagents (GE Healthcare, Chalfont St. Giles, UK) were used according to the manufacturer's instructions.

Flow cytometric analysis. To detect expression of DR5 on the cell surface, the cells ($1 \times 10^6$) were washed with PBS containing 5% FBS and incubated with 5 μg/ml TRA-8 or an isotype-specific mouse IgG1 (Southern Biotechnology Associates, Inc., Birmingham, Ala.) at 4° C. for 30 min. After washing with PBS containing 5% FBS, the cells were treated with 5 μg/ml phycoerythrin (PE)-conjugated goat anti-mouse IgG1 (Southern Biotechnology Associates, Inc.) at 4° C. for 30 min. Then, the cells were washed, fixed with 1% paraformaldehyde, and analyzed on FACScan flow cytometer and CellQuest software (BD, Franklin Lakes, N.J.).

Cell viability analysis: To examine the effect of the serum, the cells ($2 \times 10^4$) were plated onto well of a 96-well microplate and cultured in complete culture medium at 37° C. for 24 h, washed with serum-free medium, and further incubated in 100 μl of complete medium or serum-free medium at 37° C. for the indicated times. Cell viability was assessed by measurement of cellular ATP levels using ATPlite™-M luminescence assay system (PerkinElmer, Inc., Waltham, Mass.) according to the manufacturer's instructions, and determined as a percentage relative to the luminescence value of cells, which were cultured in complete medium, used as a control. The assay of cell viability was repeated in triplicate experiments. Data were statistically analyzed by the Student t test. In case of the Student t test, if variance of homogeneity was rejected ($P<0.05$ by F test), the Welch test was applied. Probability values (P-values) less than 0.05 were considered to be statistically significant. All P-values were rounded to four decimal places.

To evaluate the effect of TRA-8 in serum-free condition, the cells were cultured as described above, washed with serum-free medium and treated with or without TRA-8 or chemotherapeutic agents in 100 μl of serum-free medium at 37° C. for the indicated times. Cell viability was assessed using ATPLite™ assay (PerkinElmer, Inc., Waltham, Mass.) and determined as a percentage relative to the luminescence value of untreated cells used as a control. The assay of cell viability was repeated in triplicate experiments.

Preparation of sera from tumor-bearing mice. COLO 205 cells ($1\times10^7$) were inoculated subcutaneously into athymic nude mice on day 0. The mice were grouped randomly. Each of the groups consisted of 3 mice. TRA-8 (10 mg/kg) was administered intraperitoneally to mice on days 16 and 20. CPT-11 (33 mg/kg) was administered intravenously to mice on days 17 and 21. Length and width of solid tumors were measured twice weekly. Tumor volume ($mm^3$) was calculated as $axb^2/2$, where a and b are the length and the width (mm) of the tumor, respectively. Tumor size was determined as a percentage relative to the tumor volume on day 16. Sera were obtained from the tumor-bearing mice on day 23.

Establishment of ELISA. Female BALB/c mice were immunized with recombinant PRDX1. Lymphocytes from local lymph nodes were fused with NS-1 myeloma cells. Positive hybridomas were screened against recombinant PRDX1 by ELISA. After obtaining several antibodies, ELISA plates were coated with captured antibody and blocked with 3% BSA in PBS. Each protein was detected with biotin-conjugated antibody followed by peroxidase-conjugated streptavidin. Absorbance at 450 nm ($A_{450}$) was measured using a microplate reader. Each protein level in sera was determined as $A_{450}$ value.

Results

The anti-DR5 monoclonal antibody TRA-8 has an intrinsic agonistic activity without crosslinking agents or surface adherence, and induces apoptosis in a variety of cancer cells in vitro. In addition, TRA-8 has antitumor activity both alone and in combination with chemotherapy and/or radiation therapy in various human tumor xenograft models. However, different degrees of TRA-8 sensitivity have been observed among cancer cells, although DR5 is expressed on the cells. No biomarker currently exists for prediction of TRA-8 effect.

Proteins may be released or secreted from cancer cells during apoptosis and resulting changed levels of these proteins may reflect the response of cancer cells to therapeutic agents. It is possible that these proteins can be used as biomarkers to monitor and predict the effect of therapeutic agents such as, for example, TRA-8. To discover such proteins, 2-DE coupled with MS was selected from some proteomic technologies to focus on relative abundant proteins. Since it was determined that human colon cancer cell line COLO 205 expresses DR5 on the surface and is one of the most sensitive cell lines to TRA-8, this cell line was used to discover proteins released from TRA-8-sensitive cells. Released or secreted proteins are valuable as potential biomarkers because these proteins are detected in the sera or plasma of patients, which are readily accessible samples. After culture supernatants for TRA-8-treated COLO 205 cells were resolved by 2-DE with subsequent staining with SYPRO Ruby, proteomic profiles of the culture supernatants were obtained based on comparison among gels using PDQUEST® 2-D analysis software (FIG. 1). We found that 6 protein spots emerged in the culture supernatants upon treatment of TRA-8. These proteins were identified as PGK1, ALDOA, proteasome subunit beta type 1 (PSB1), PRDX1, COF1, and histone H4 by MS (Table 2). These data suggest that these proteins, which are released from COLO 205 cells into the culture supernatant upon TRA-8 treatment, are biomarkers to monitor the cytotoxic effect of the antibody.

For the purpose of biomarker discovery for predicting the sensitivity of cancer cells to anti-cancer drug, anti-DR5 antibody (TRA-8) was used as an anti-cancer drug. A panel of 15 human colon cancer cell lines was screened for in vitro susceptibility to TRA-8-mediated apoptosis (Table 1). To determine the profile of the released proteins during TRA-8-mediated apoptosis, COLO 205 cells were selected for initial screening as they were very susceptible to TRA-8 treatment. After COLO205 human colon cancer cells were treated with or without TRA-8, the culture supernatants were resolved by two-dimensional gel electrophoresis and the differentially expressed proteins that released from control and TRA-8-treated COLO 205 cells were determined using PDQuest 2-D analysis software (FIG. 1). There was an increase in the released proteins with increased dose of TRA-8 treatment compared to that of untreated cells (FIG. 1, circles). Mass spectrometry analysis indicated that these newly released proteins in the culture supernatant of TRA-8-treated COLO205 cells were fructose-bisphosphate aldolase A (ALDOA), cofilin 1 (COF1), histone H4, phosphoglycerate kinase 1 (PGK1), and peroxiredoxin 1 (PRDX1) (Table 2). The increased expression levels of these proteins was further confirmed by Western blot analysis using specific antibodies.

TABLE 1

| Colon Cancer Cell line | IC$_{50}$ of TRA-8 (ng/ml) | |
|---|---|---|
| | Sequential | Simultaneous |
| COLO 205 | 1.22 | 0.322 |
| SW480 | 4.01 | 1.56 |
| HCT116 | 9.04 | 1.91 |
| SW948 | 12.6 | 0.51 |
| HCT15 | 17.8 | 3.56 |
| DLD1 | 19.8 | 1.21 |
| SW403 | 65.7 | 1.07 |
| SW1116 | 68.7 | 10.4 |
| WiDr | 87.3 | 14.8 |
| LS174T | 2,250 | 16.4 |
| T84 | >10,000 | 79.1 |
| HT-29 | >10,000 | 106 |
| SW620 | >10,000 | >10,000 |
| Caco2 | >10,000 | >10,000 |
| SNUC1 | >10,000 | >10,000 |

Sequential Method: spread cells→37° C./24 h, add antibody→37° C./24 h, assay cell viability
Simultaneous Method: spread cells, add antibody→37° C./24 h, assay cell viability

TABLE 2

| Protein Name | Accession No. | Mascot score | Matched peptides | MW (kD) | pI |
|---|---|---|---|---|---|
| Fructose-bisphosphate aldolase A (ALDOA) | P04075 | 1200 | 53 | 39.3 | 8.39 |
| Cofilin-1 (COF1) | P23528 | 813 | 30 | 18.4 | 8.26 |
| Histone H4 | P62805 | 280 | 4 | 11.2 | 11.36 |
| Phosphoglycerate kinase 1 (PGK1) | P00558 | 1166 | 44 | 44.5 | 8.30 |
| Peroxiredoxin 1 (PRDX1) | Q06830 | 486 | 16 | 22.1 | 8.27 |
| Proteasome subunit beta type 1 (PSMB1) | P20618 | 451 | 18 | 26.5 | 8.27 |

Figure 2A:
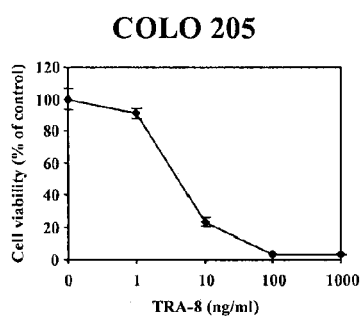
FIG. 2A shows COLO 205, WiDr, and HT-29 cells treated with none or TRA-8 at a final concentration of 1, 10, 100, or 1000 ng/ml at 37° C. for 24 h. Cell viability was assessed by measurement of cellular ATP levels and determined as a percentage relative to the luminescence value of untreated cells used as a control. Each point and bar represents the mean and standard error of cell viability on triplicate experiments, respectively.
Figure 2A:
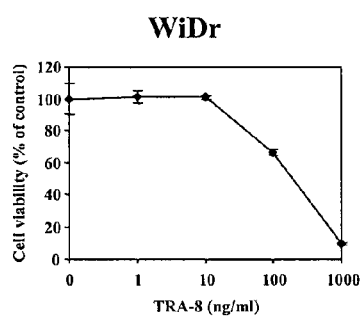
Figure 2A:
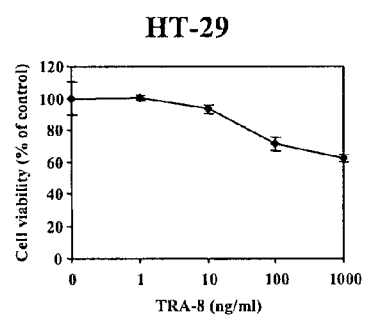
Figure 2B:
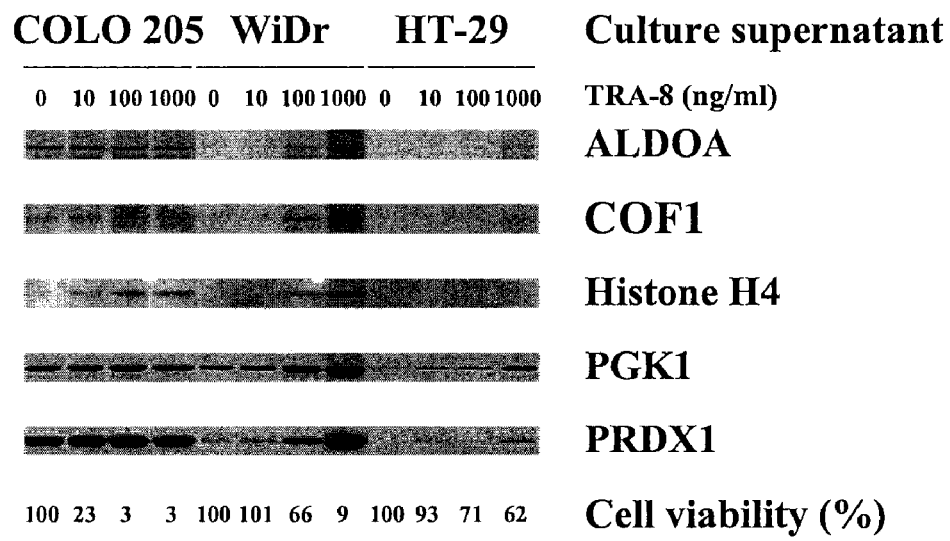
FIG. 2B shows COLO 205, WiDr and HT-29 cells treated with none or TRA-8 at a final concentration of 1, 10, 100, or 1000 ng/ml at 37° C. for 24 h. Culture supernatants were resolved by SDS-PAGE, followed by immunoblotting with anti-ALDOA, anti-COF1, anti-histone H4, anti-PGK1, or anti-PRDX1 antibodies. Cell viabilities are shown on the bottom.

To determine whether these identified proteins in COLO205 cell culture is correlated with TRA-8 susceptibility of tumor cells, three human colon cell lines, COLO205, WiDr and HT29, which represent a different susceptibility to TRA-8-mediated apoptosis, were selected. Since the cells were treated with TRA-8 in the serum-starved condition, the effect of the serum starvation on cell viability was examined. The serum starvation had little or no effect on cell viability of three cell lines, and the pattern of TRA-8 susceptibility among the three cell lines was not altered (FIG. 2A). The baseline levels of the released proteins were significantly different among the three cell lines, which appeared to be correlated with the susceptibility of tumor cell to TRA-8-mediated apoptosis. Highly susceptible COLO205 cells released the highest baseline levels of ALDOA, COF1, PGK1 and PRDX1. The TRA-8 intermediate susceptible cells, WiDr, released the baseline levels of two proteins, PGK1 and PRDX1, whereas TRA-8 resistant cells, HT29, did not release any detectable baseline levels of these proteins (FIG. 2B). Upon treatment with different doses of TRA-8, the release of all five proteins from COLO205 cells into the culture supernatants was increased by incubation with a very low dose (10 ng/ml) of TRA-8. A significant increase of these proteins was observed in WiDr cells upon the higher doses (>100 ng/ml) of TRA-8 treatment. In contrast, the TRA-8 resistant HT29 cells did not release significant levels of these proteins at low doses of TRA-8 treatment (except PGK1), and high doses (1 μg/ml) of TRA-8 were required for the release of COF1 and PRDX1. These results suggest that both baseline and TRA-8-induced levels of these proteins may be correlated with the susceptibility of tumor cells to TRA-8-mediated apoptosis.

Figure 3A:
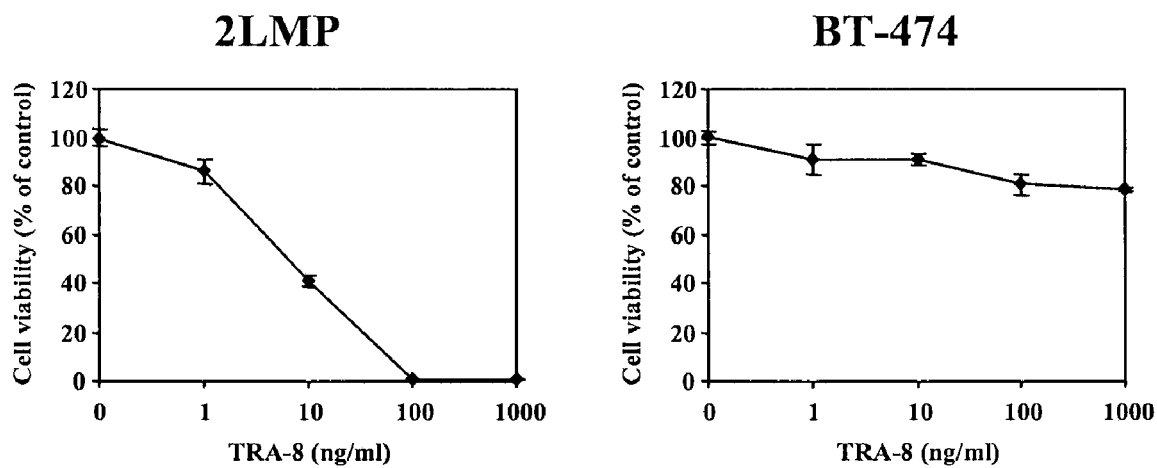
FIG. 3A shows 2LMP and BT-474 cells treated with none or TRA-8 at a final concentration of 1, 10, 100, or 1000 ng/ml at 37° C. for 24 h. Cell viability was determined as described in FIG. 2A.
Figure 3B:
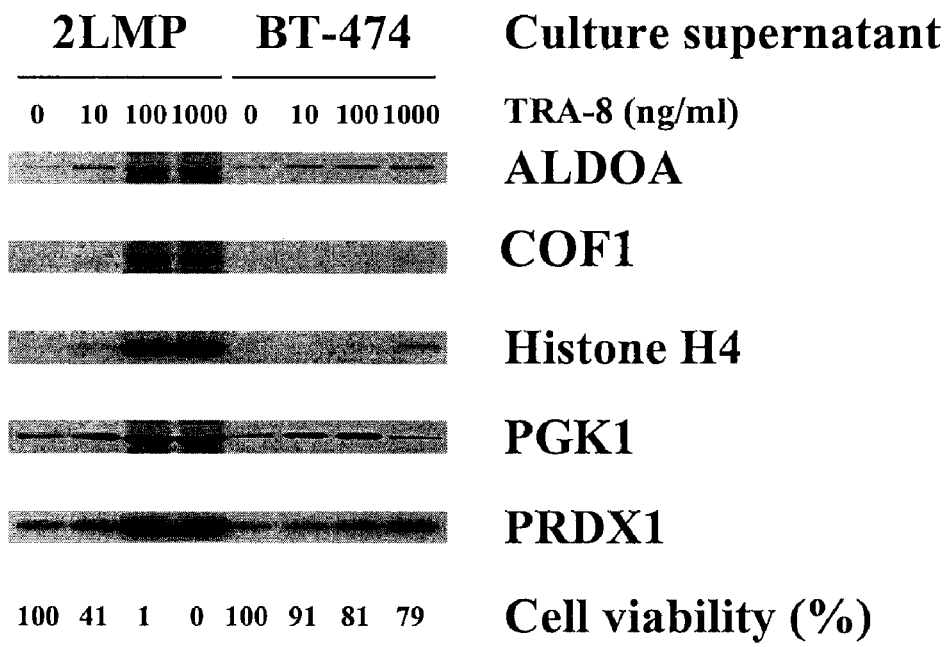
FIG. 3B shows cells treated with none or TRA-8 at a final concentration of 1, 10, 100, or 1000 ng/ml at 37° C. for 24 h. Culture supernatants were analyzed as described in FIG. 2B. Cell viabilities are shown on the bottom.

To determine whether these identified proteins are universal for other types of human cancer cells, the alteration of these proteins were examined in 2LMP and BT-474 human breast cancer cell lines. Serum starvation had little effect on cell viability of 2LMP (96%) and BT-474 (87%). In this condition, TRA-8 had a significant cytotoxic effect on 2LMP cells, but not on BT-474 cells (FIG. 3A). Upon treatment of 2LMP cells with TRA-8, release of ALDOA, COF1, histone H4, PGK1, and PRDX1 into the culture supernatant was significantly increased (FIG. 3B). When BT-474 cells were treated with TRA-8, the increase of ALDOA and PRDX1 was detected. Only upon treatment with a high concentration of TRA-8 (1 μg/ml) was the increase of COF1 and histone H4 in the culture supernatant shown. PGK1 was increased minimally in the culture supernatant. These data demonstrate that release of ALDOA, COF1, histone H4, PGK1 and PRDX1 is related to cytotoxic efficacy of anti-DR5 antibody on human breast cancer cells.

Figure 4A:
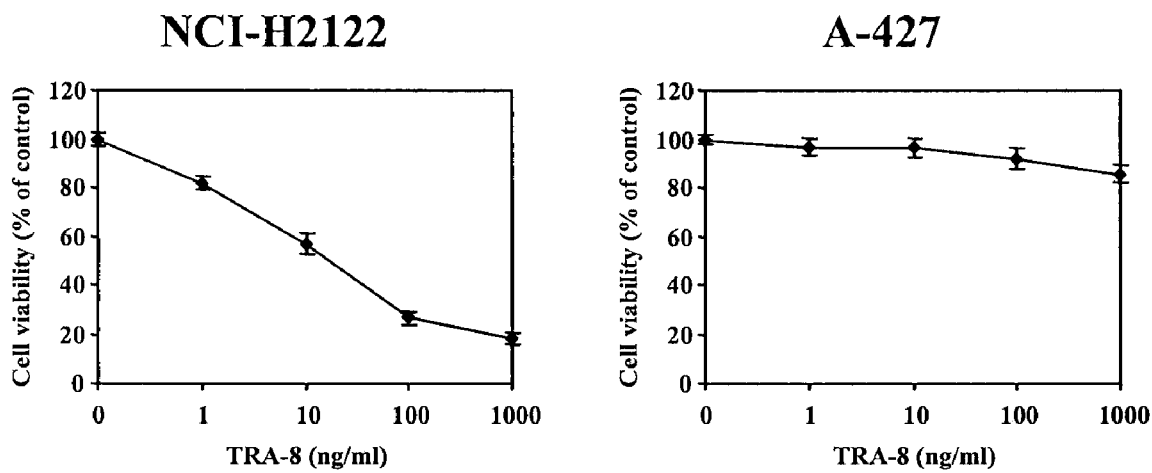
FIG. 4A shows NCI-H2122 and A-427 cells treated with none or TRA-8 at a final concentration of 1, 10, 100, or 1000 ng/ml at 37° C. for 24 h. Cell viability was determined as described in FIG. 2A.
Figure 4B:
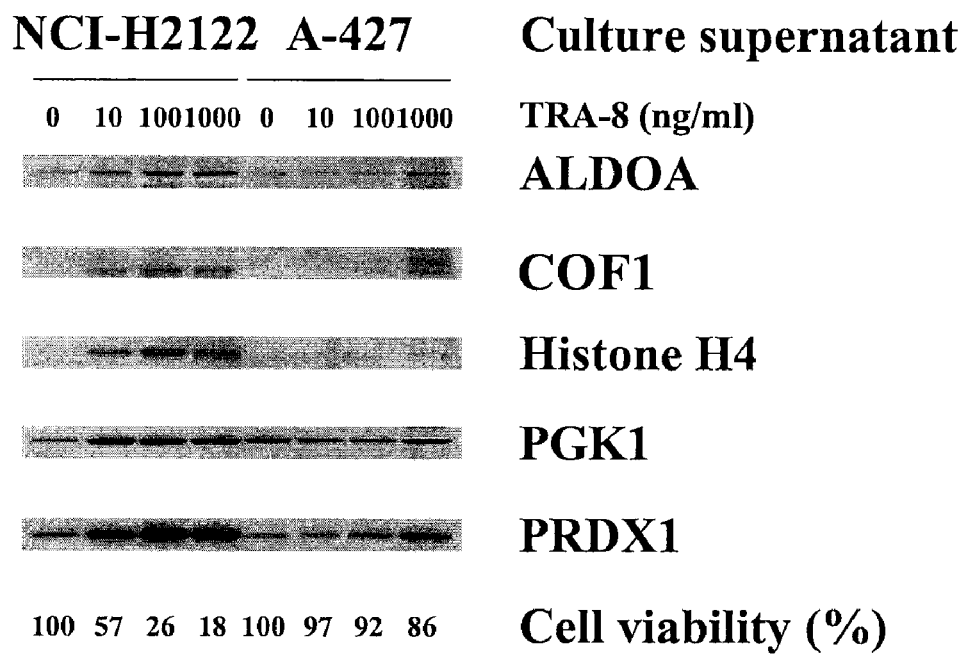
FIG. 4B shows cells treated with none or TRA-8 at a final concentration of 1, 10, 100, or 1000 ng/ml at 37° C. for 24 h. Culture supernatants were analyzed as described in FIG. 2B. Cell viabilities are shown on the bottom.

Next, human lung cancer cell lines NCI-H2122 and A-427 were utilized. As with human colon and breast cancer cells, serum starvation had little effect on cell viability of NCI-H2122 (87%) and A-427 (82%). As shown in FIG. 4A, TRA-8 had a significant cytotoxic effect on NCI-H2122 cells in this condition, but not on A-427 cells. Upon treatment of TRA-8, release of ALDOA, COF1, histone H4, PGK1, and PRDX1 into the culture supernatant was increased from NCI-H2122 cells (FIG. 4B). When A-427 cells were treated with TRA-8, the increase of PRDX1 was detected. Only upon treatment of TRA-8 at a final concentration of 1 μg/ml was the increase of ALDOA, COF1 and histone H4 in the culture supernatant shown. PGK1 was increased slightly in the culture supernatant. These results indicate that release of ALDOA, COF1, histone H4, PGK1 and PRDX1 is correlated with cytotoxic efficacy of anti-DR5 antibody on human lung cancer cells.

Figure 5A:
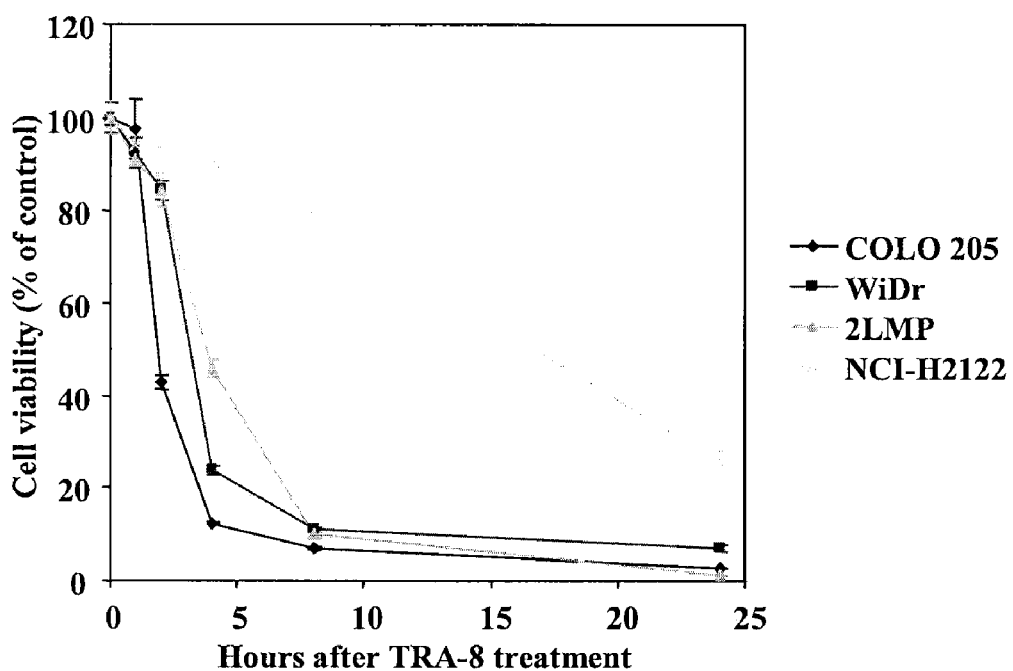
FIG. 5A shows COLO 205 (diamonds), WiDr (squares), 2LMP (triangles), and NCI-H2122 cells (crosses) treated with or without TRA-8 at a final concentration of 1 µg/ml at 37° C. for 0, 1, 2, 4, 8, or 24 h. Cell viability was determined as described in FIG. 2A.
Figure 5B:
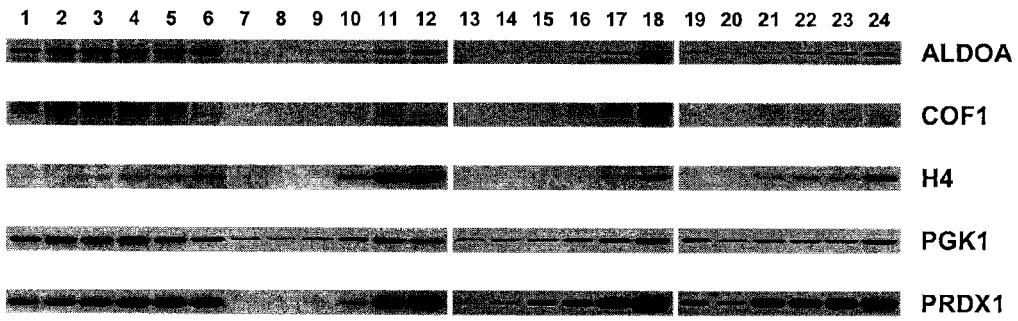
FIG. 5B shows COLO 205 cells (lanes 1-6), WiDr cells (lanes 7-12), 2LMP cells (lanes 13-18) and NCI-H2122 cells (lanes 19-24) incubated with TRA-8 at a final concentration of 1 µg/ml in serum-free conditions at 37° C. for 0 (lanes 1, 7, 13 and 19), 1 hour (lanes 2, 8, 14 and 20), 2 hours (lanes 3, 9, 15 and 21), 4 hours (lanes 4, 10, 16 and 22), 8 hours (lanes 5, 11, 17 and 23) and 24 hours (lanes 6, 12, 18 and 24). The culture supernatants were resolved by SDS-PAGE followed by immunoblotting with antibodies against ALDOA, COF1, histone H4, PGK1 or PRDX1.

When the time courses of candidate biomarkers were analyzed in the culture supernatant after TRA-8 treatment, the biomarkers were sensitive enough to predict the efficacy of TRA-8 (FIG. 5). ALDOA, COF1, histone H4, PGK1 and PRDX1 were identified as potential biomarkers to monitor TRA-8 effect using human cancer cells, on which various degrees of TRA-8 sensitivity was observed. To examine how early these released molecules can be detected upon TRA-8 treatment, TRA-8-sensitive cell lines COLO 205, WiDr, 2LMP, and NCI-H2122 were utilized. As shown in FIG. 5A, TRA-8 had a significant cytotoxic effect on these cell lines in a time-dependent manner. Since growth of NCI-H2122 cells is slower than other ones, it was shown that the TRA-8 effect on NCI-H2122 cells seems to be weaker than on other TRA-8-sensitive cells. During TRA-8-mediated apoptosis, all candidate biomarkers were released from the cells in a time-dependent manner, although degrees of released biomarkers varied among the cells (FIG. 5B). Increase of released ALDOA and PRDX1 was observed after 1 or 2 hours of TRA-8 treatment, while TRA-8 did not show a significant effect on the cell viability at these time points. Although other molecules were also increased upon TRA-8 treatment, released levels of COF1 and H4 were low at early time points, and changes in released PGK1 were small. These results suggest that ALDOA and PRDX1 are more sensitive and detectable biomarkers to predict cytotoxic effect of TRA-8 among candidate biomarkers.

Figure 6A:
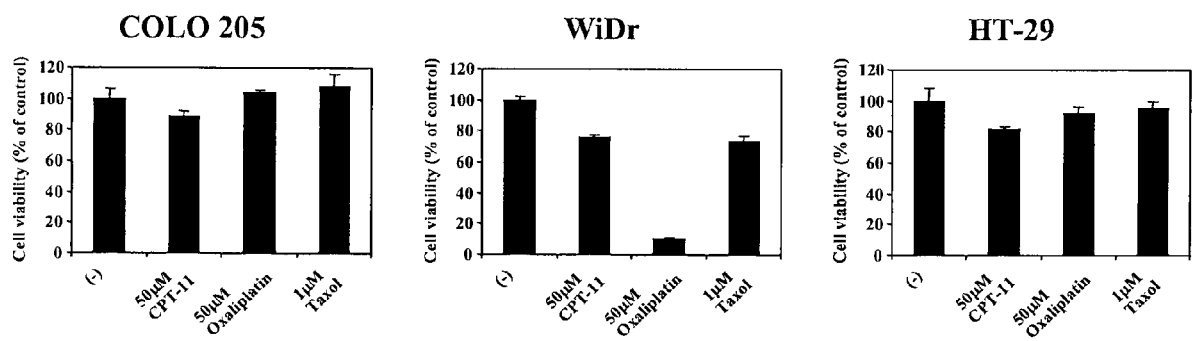
FIG. 6A shows COLO 205, WiDr and hT-29 cells treated with media alone (condition 1), 50 µM CPT-11 (condition 2), 50 µM oxaliplatin (condition 3) or 1 µM paclitaxel (condition 4) at 37° C. for 24 (open bars) and 48 hours (solid bars) in serum-free conditions. Cell viability was determined as described in FIG. 2A. Cell viability analysis was performed using the ATPLite™ assay (PerkinElmer, Inc., Waltham, Mass.). Each column and bar represent the mean and standard error of the data of triplicate experiments, respectively.
Figure 6B:
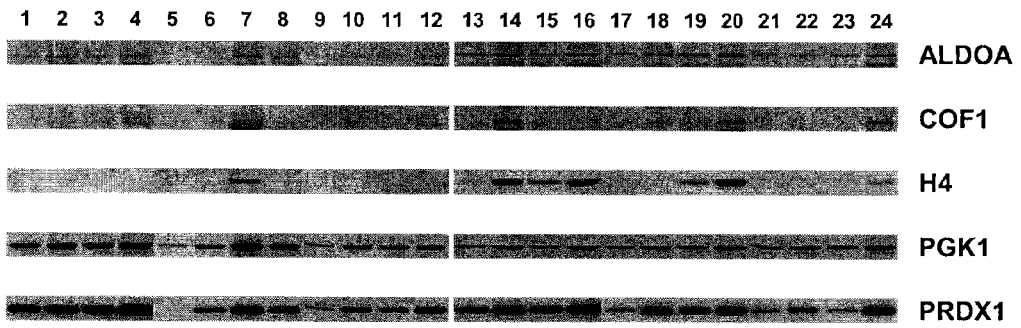
FIG. 6B shows COLO 205 cells (lanes 1-4 and 13-16), WiDr cells (lanes 5-8 and 17-20) and HT-29 cells (Lanes 9-12 and 21-24) incubated with media alone (lanes 1, 5, 9, 13, 17 and 21), 50 µM CPT-11 (lanes 2, 6, 10, 14, 18 and 22), 50 µM oxaliplatin (lanes 3, 7, 11, 15, 19 and 23) or 1 µM paclitaxel (lanes 4, 8, 12, 16, 20 and 24) at 37° C. for 24 hours (lanes 1-12) and 48 hours (lanes 13-24) in serum-free conditions. The culture supernatants were resolved by SDS-PAGE followed by immunoblotting with the antibodies against ALDOA, COF1, histone H4, PGK1 or PRDX1 as described in FIG. 2B.

Next, the effect of chemotherapy agents on candidate biomarkers was assessed. Some chemotherapeutic agents need a long term incubation to achieve a cytotoxic effect on the cells. Serum starvation for 24 h had minimal effect on cell viability of COLO 205, WiDr, and HT-29. In contrast, serum starvation for 48 h had an effect on the cells. In this condition, CPT-11, oxaliplatin, and paclitaxel were used as chemotherapeutic agents. When the cells were treated with chemotherapeutic agents for 24 h, oxaliplatin had a significant effect on WiDr cells (FIG. 6A). CPT-11 killed 71% of COLO 205 cells, oxaliplatin killed 41% of COLO 205 cells and 99% of WiDr cells and paclitaxel killed 62% of COLO 205 cells and 72% of WiDr cells. Immunoblotting showed that release of ALDOA, COF1, histone H4, PGK1 and PRDX1 into the culture supernatant were increased upon treatment of oxaliplatin (FIG. 6B). On incubation with chemotherapeutic agents for 48 h, oxaliplatin and paclitaxel affected cell viability of COLO 205 and WiDr cells, and CPT-11 had a significant effect on COLO 205 cells (FIG. 6C). In this condition, levels of ALDOA, COF1, histone H4, PGK1 and PRDX1 detected in the culture supernatant were dependent on cytotoxic effect of the chemotherapeutic agents (FIG. 6D). Increase of released biomarkers from the cells correlated with the cytotoxic effect of chemotherapy agents. These data demonstrate ALDOA, COF1, histone H4, PGK1 and PRDX1 are useful as biomarkers to predict cytotoxic efficacy of chemotherapeutic agents on human cancer cells.

To determine whether cancer cells and tissues expressed high levels of PRDX1 and PGK1, a panel of monoclonal antibodies against these proteins was developed. Western blot analysis using a panel of human cancer cell lines demonstrated that all tested human cancer cells expressed high levels of PRDX1 (FIG. 7A) and PGK1 (FIG. 7B). Immunohistological staining of a panel of human ovarian cancer tissues shows that cancer cells selectively expressed high levels of PGK1 (FIG. 7C). The correlation of PGK1 expression levels and other apoptosis proteins with TRA-8-mediated apoptosis of ascites-derived cancer cells and chemotherapy response of the patients is summarized in Table 3.

TABLE 3

| | Sensitivity | | Expression | | | | | | | |
|---|---|---|---|---|---|---|---|---|---|---|
| No | TRA-8 | cisplatin | DR5 | PGK1 | cIAP1 | cIAP2 | XIAP | Bcl-2 | Bcl-XL | Bax |
| 1 | + | + | + | + | ++++ | ++++ | ++ | + | + | + |
| 2 | + | − | ++ | ++ | ++++ | ++++ | +++ | − | +++ | ++ |
| 3 | +++ | + | +++ | +++ | ++++ | ++++ | +++ | + | +++ | +++ |
| 4 | +++ | + | ++ | ++++ | ++++ | ++++ | ++++ | ++ | +++ | ++ |
| 5 | +++ | + | +++ | ++++ | ++++ | ++ | + | ++++ | − | +++ |
| 6 | +++ | ? | ++ | ++++ | ++++ | ++++ | ++++ | + | ++++ | +++ |

To determine if the biomarkers are useful to monitor and predict efficacy of agents in vivo, COLO 205 tumor-bearing mice were used to examine if candidate biomarkers can predict the efficacy of anti-cancer drug on COLO 205 tumor in vivo. After TRA-8 and/or CPT-11 were administered twice a week to COLO 205 tumor-bearing mice for only one week, sera were retrieved from the mice and analyzed by ELISA. While TRA-8 or TRA-8 plus CPT-11 had slight antitumor efficacy, CPT-11 alone showed not antitumor effects (FIG. 8A). The amount of ALDOA, PGK1, and PRDX1 in the sera was increased by concomitant administration of TRA-8 or TRA-8 plus CPT-11 (FIG. 8B). Thus, ALDOA, COF1, histone H4, PGK1, PRDX1, or a combination thereof are useful as biomarkers to predict the sensitivity of cancer cells to anti-cancer drug.

Disclosed are materials, compositions, and components used for, used in conjunction with, used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a biomarker is disclosed and discussed and a number of modifications that can be made to a number of molecules including the biomarker are discussed, each and every combination and permutation of the biomarker and the modifications that are possible are specifically contemplated unless specifically indicated to the contrary. Thus, if a class of molecules A, B, and C are disclosed as well as a class of molecules D, E, and F and an example of a combination molecule, A-D, is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms a, an, and the include plural reference unless the context clearly dictates otherwise. Thus, for example, reference to a biomarker includes a plurality of such biomarkers, reference to the biomarker is a reference to one or more biomarkers and equivalents thereof known to those skilled in the art, and so forth.

Optional or optionally means that the subsequently described event, circumstance, or material may or may not occur or be present, and that the description includes instances where the event, circumstance, or material occurs or is present and instances where it does not occur or is not present.

Unless defined otherwise, all technical and scientific terms used herein have the same meanings as commonly understood by one of skill in the art to which the disclosed method and compositions belong. Publications cited herein and the material for which they are cited are hereby specifically incorporated by reference. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word comprise and variations of the word, such as comprising and comprises, means including but not limited to, and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A method of predicting sensitivity of a cancer cell to a first anti-cancer agent comprising:
    (a) contacting the cancer cell with an effective amount of the anti-cancer agent, wherein the anti-cancer agent comprises TRA-8 or an antibody having the same epitope specificity as TRA-8; and
    (b) evaluating the release by the cell of one or more biomarkers selected from the group consisting of fructose-bisphosphate aldolase A (ALDOA), phosphoglycerate kinase 1 (PGK1), peroxiredoxin 1 (PRDX1), and colfilin 1 (COF1), an increase in release by the contacted cell compared to a control cell indicating that the cancer cell is sensitive to the agent.

2. The method of claim 1, wherein the cancer cell is contacted in vivo.

3. The method of claim 1, wherein the cancer cell is contacted in vitro.

4. The method of claim 1, wherein the antibody having the same epitope specificity as TRA-8 is a humanized version of TRA-8.

5. A method of determining an effective dose for an anti-cancer agent comprising:
   (a) contacting one or more cancer cells with a plurality of dosages of the anti-cancer agent under conditions that allow cellular release of one or more biomarkers selected from the group consisting of fructose-bisphosphate aldolase A (ALDOA), phosphoglycerate kinase 1 (PGK1), peroxiredoxin 1 (PRDX1), and colfilin 1 (COF1), and histone H4, wherein the anti-cancer agent comprises TRA-8 or an antibody having the same epitope specificity as TRA-8; and
   (b) detecting the release at each dosage, higher release rates indicating an effective dosage.

6. The method of claim 5, wherein the antibody having the same epitope specificity as TRA-8 is a humanized version of TRA-8.

7. The method of claim 5, wherein at least one cell is contacted with more than one dosage.

8. The method of claim 5, wherein each cell is contacted with only one dosage.

9. The method of claim 1, wherein the method further comprises evaluating the release by the cell of histone H4, an increase in release by the contacted cell compared to a control cell indicating that the cancer cell is sensitive to the agent.

* * * * *

UNITED STATES PATENT AND TRADEMARK OFFICE
CERTIFICATE OF CORRECTION

PATENT NO. : 8,119,355 B2
APPLICATION NO. : 12/723113
DATED : February 21, 2012
INVENTOR(S) : Robert P. Kimberly, Tong Zhou and Takeshi Isoyama It is certified that error appears in the above-identified patent and that said Letters Patent is hereby corrected as shown below:

Column 33, line 8, "(PRDX1), and colfilin 1" should read --(PRDX1), colfilin 1--

Signed and Sealed this
Seventeenth Day of April, 2012

David J. Kappos
*Director of the United States Patent and Trademark Office*